US011197928B2

(12) United States Patent
Huda

(10) Patent No.: US 11,197,928 B2
(45) Date of Patent: Dec. 14, 2021

(54) SUSTAINED PRODUCTION OF HIGH AFFINITY ANTIGEN SPECIFIC ANTIBODY BY HIGH DOSE BAFF RECEPTOR-TARGETING MAB-SIRNA CONJUGATE

(71) Applicant: Board of Regents, The University of Texas System, Austin, TX (US)

(72) Inventor: Ruksana Huda, League City, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 345 days.

(21) Appl. No.: 15/868,912

(22) Filed: Jan. 11, 2018

(65) Prior Publication Data

US 2018/0296666 A1 Oct. 18, 2018

Related U.S. Application Data

(60) Provisional application No. 62/446,204, filed on Jan. 13, 2017.

(51) Int. Cl.
| | |
|---|---|
| *A61K 39/39* | (2006.01) |
| *C07K 16/28* | (2006.01) |
| *C07K 14/47* | (2006.01) |
| *G01N 33/68* | (2006.01) |
| *C12N 15/113* | (2010.01) |
| *C07K 14/705* | (2006.01) |
| *G01N 33/564* | (2006.01) |
| *A61K 39/00* | (2006.01) |

(52) U.S. Cl.
CPC .............. *A61K 39/39* (2013.01); *C07K 14/47* (2013.01); *C07K 14/70578* (2013.01); *C07K 16/2875* (2013.01); *C12N 15/1138* (2013.01); *G01N 33/564* (2013.01); *G01N 33/6854* (2013.01); *G01N 33/6863* (2013.01); *G01N 33/6866* (2013.01); *G01N 33/6869* (2013.01); *A61K 2039/545* (2013.01); *A61K 2039/55561* (2013.01); *A61K 2039/6056* (2013.01); *C07K 2317/24* (2013.01); *C07K 2317/92* (2013.01); *C07K 2319/09* (2013.01); *C07K 2319/10* (2013.01); *C12N 2310/122* (2013.01); *C12N 2310/14* (2013.01); *C12N 2310/3513* (2013.01); *C12N 2310/531* (2013.01); *G01N 2333/5406* (2013.01); *G01N 2333/5428* (2013.01); *G01N 2333/57* (2013.01); *G01N 2500/00* (2013.01); *G01N 2800/24* (2013.01); *G01N 2800/52* (2013.01)

(58) Field of Classification Search
CPC ....................................................... A61K 39/39
USPC .................................................... 424/134.1
See application file for complete search history.

(56) References Cited

U.S. PATENT DOCUMENTS

| | | | |
|---|---|---|---|
| 5,138,045 A | 8/1992 | Cook et al. | |
| 5,212,295 A | 5/1993 | Cook | |
| 5,218,105 A | 6/1993 | Cook et al. | |
| 5,223,168 A | 6/1993 | Holt | |
| 5,378,825 A | 1/1995 | Cook et al. | |
| 5,386,023 A | 1/1995 | Sanghvi et al. | |
| 5,457,191 A | 10/1995 | Cook et al. | |
| 5,459,255 A | 10/1995 | Cook et al. | |
| 5,506,351 A | 4/1996 | McGee | |
| 5,521,302 A | 5/1996 | Cook | |
| 5,539,082 A | 7/1996 | Nielsen et al. | |
| 5,541,307 A | 7/1996 | Cook et al. | |
| 5,554,746 A | 9/1996 | Ravikumar et al. | |
| 5,571,902 A | 11/1996 | Ravikumar et al. | |
| 5,578,718 A | 11/1996 | Cook et al. | |
| 5,587,361 A | 12/1996 | Cook et al. | |
| 5,587,469 A | 12/1996 | Cook et al. | |
| 5,587,470 A | 12/1996 | Cook et al. | |
| 5,602,240 A | 2/1997 | Mesmaeker et al. | |
| 5,608,046 A | 3/1997 | Cook et al. | |
| 5,610,289 A | 3/1997 | Cook et al. | |
| 5,693,762 A * | 12/1997 | Queen ................... | C07K 16/00 |
| | | | 424/133.1 |
| 5,999,797 A | 12/1999 | Zancho et al. | |
| 6,262,241 B1 | 7/2001 | Cook et al. | |
| 8,106,163 B2 | 1/2012 | Heusser et al. | |
| 9,006,416 B2 | 4/2015 | Rossi et al. | |
| 2002/0132990 A1 | 9/2002 | Huston et al. | |
| 2004/0023902 A1 | 2/2004 | Marasco et al. | |
| 2010/0209440 A1 | 8/2010 | Shankar et al. | |
| 2016/0279237 A1 | 9/2016 | Miller et al. | |
| 2016/0310590 A1 | 10/2016 | O'Hagan et al. | |

FOREIGN PATENT DOCUMENTS

| | | |
|---|---|---|
| WO | 2009083738 A2 | 8/2009 |
| WO | 2015100246 A1 | 7/2015 |

OTHER PUBLICATIONS

Kyaw et al (PLOS ONE, 2013, 8(4)(e60430): 1-12).*
Zhou et al (Methods in Molecular Biology, 2015, v1297: 169-185).*
Aricha, R., et al., "Blocking of IL-6 suppresses experimental autoimmune myasthenia gravis." J Autoimmun. (2011), 36(2):135-41.
Balasa, B., et al., "The Th2 cytokine IL-4 is not required for the progression of antibody-dependent autoimmune myasthenia gravis." J Immunol. (1998), 161(6):2856-62.
Benveniste, E.N., et al., "Type I interferons as anti-inflammatory mediators." Sci STKE. (2007), 406:pe70.

(Continued)

*Primary Examiner* — Sean E Aeder
(74) *Attorney, Agent, or Firm* — Edwin S. Flores; Daniel J. Chalker; Chalker Flores, LLP

(57) ABSTRACT

The present invention includes a composition and a method of modulating an immune response with a composition that comprises an anti-BAFF receptor antibody or binding fragment thereof that is bound or conjugated to an siRNA, and shRNA, or both, that targets a BAFF receptor mRNA.

28 Claims, 14 Drawing Sheets

Specification includes a Sequence Listing.

(56) References Cited

OTHER PUBLICATIONS

Cao, Y., et al., "Autoreactive T Cells from Patients with Myasthenia Gravis Are Characterized by Elevated IL-17, IFN-γ, and GM-CSF and Diminished IL-10 Production." J Immunol. (2016), 196(5):2075-84.
Cufi, P., et al., "Central role of interferon-beta in thymic events leading to myasthenia gravis." J Autoimmun. (2014), 52:44-52.
Fattom et al., "Comparative Immunogenicity of Conjugates Composed of the *Staphylococcus aureus* Type 8 Capsular Polysaccharide Bound to Carrier Proteins by Adipic Acid Dihydrazide or N-Succinimidyl-3-(2-Pyridyldithio)propionate." Infection & Immun. (1992), 60:584-589.
Fu, L., et al., "BAFF-R promotes cell proliferation and survival through interaction with IKK beta and NF-kappa B/c-Rel in the nucleus of normal and neoplastic B-lymphoid cells." Blood. (2009), 113(19):4627-36.
Goldmacher et al., "Photoactivation of Toxin Conjugates," Bioconj. Chem. (1992), 3:104-107.
Hazum et al., "A Photocleavable Protecting Group fro the Thiol Function of Cysteine," Proc. Eur. Pept. Symp., 16th, Brunfeldt, K (Ed), (1981), pp. 105-110, 1981.
Huda, R., et al., "Complement C2 siRNA mediated therapy of myasthenia gravis in mice." J Autoimmun. (2013), 42:94-104.
Huda, R., et al., "Targeting complement system to treat myasthenia gravis." Rev Neurosci. (2014), 25(4):575-83.
Iyer, S.S., et al. "Role of interleukin 10 transcriptional regulation in inflammation and autoimmune disease." Crit Rev Immunol. (2012), 32(1):23-63.
Koncz, G., et al., "The Fas/CD95 Receptor Regulates the Death of Autoreactive B Cells and the Selection of Antigen-Specific B Cells." Front Immunol. (2012), 3:207.
Lindstrom, J.M., et al., "Antibody to acetylcholine receptor in myasthenia gravis: prevalence, clinical correlates, and diagnostic value." Neurology. (1976), 26:1054-9.
Lövgren, T., et al., "Induction of interferon-alpha production in plasmacytoid dendritic cells by immune complexes containing nucleic acid released by necrotic or late apoptotic cells and lupus IgG." Arthritis Rheum. (2004), 50(6):1861-72.
Margry, B., et al., "Peritoneal cavity B-1a cells promote peripheral CD4+ T-cell activation." Eur J Immunol. (2013), 43(9):2317-26.
Mehta, G., et al., "A New Approach for the Treatment of Arthritis in Mice with a Novel Conjugate of an Anti-C5aR1 Antibody and C5 Small Interfering RNA." J Immunol. (2015), 194(11):5446-54.
Naito, Y., et al., "Germinal center marker GL7 probes activation-dependent repression of N-glycolylneuraminic acid, a sialic acid species involved in the negative modulation of B-cell activation." Mol Cell Biol. (2007), 27(8):3008-22.
Ng, L.G., et al., "B cell-activating factor belonging to the TNF family (BAFF)-R is the principal BAFF receptor facilitating BAFF costimulation of circulating T and B cells." J Immunol. (2004), 173(2):807-17.
Ostlie, N., et al., "Absence of IL-4 facilitates the development of chronic autoimmune myasthenia gravis in C57BL/6 mice." J Immunol (2003), 170(1):604-12.
Peer, D., et al., "Selective gene silencing in activated leukocytes by targeting siRNAs to the integrin lymphocyte function-associated antigen-1." Proc Natl Acad Sci U S A. (2007), 104(10):4095-100.
Rauch, M., et al., "Crucial role for BAFF-BAFF-R signaling in the survival and maintenance of mature B cells." PLoS One. (2009), 4(5):e5456.
Senter et al., "Novel Photocleavable Protein Crosslinking Reagents and Their Use in the Preparation of Antibody-Toxin Conjugates." Photochem. Photobiol. (1985). 42(3):231-237.
Song, E., et al., "Antibody mediated in vivo delivery of small interfering RNAs via cell-surface receptors." Nat Biotechnol. (2005), 23(6):709-17.
Stetson, D.B., et al. "Type I interferons in host defense." Immunity. (2006), 25(3):373-81.
Sun, F., et al., "Interleukin-10 producing-B cells and their association with responsiveness to rituximab in myasthenia gravis." Muscle Nerve. (2014), 49(4):487-94.
Tian, G., et al., "Targeting IL-10 in auto-immune diseases." Cell Biochem Biophys. (2014), 70(1):37-49.
Toloue, M.M., et al., "Antibody targeted siRNA delivery." Methods Mol Biol. (2011), 764:123-39.
Tüzün, E., et al., "Complement and cytokine based therapeutic strategies in myasthenia gravis." J Autoimmun. (2011), 37(2):136-43.
Wellhoner et al., "Uptake and Concentration of Bioactive Macromolecules by K562 Cells via the Transferrin Cycle Utilizing an Acid-labile Transferrin Conjugate." J. Biol. Chem. (1991), 266:4309 4314.
Wu, B., et al., "Experimental autoimmune myasthenia gravis in the mouse." Curr Protoc Immunol. (2013), Chapter 15, Unit 15.8:1-26.
Yan M., et al., "Identification of a novel receptor for B lymphocyte stimulator that is mutated in a mouse strain with severe B cell deficiency." Curr Biol. (2001), 11(19):1547-52.
Yen et al., "Optically controlled ligand delivery. I: Synthesis of water-soluble copolymers containing photocleavage bonds." Makromol. Chem (1989), 190:69 82.
Zhao, Y., et al., "Promotion of Fas-mediated apoptosis in Type II cells by high doses of hepatocyte growth factor bypasses the mitochondrial requirement." J Cell Physiol. (2007), 213 (2):556-63.
Zitvogel, L., et al., "Type I interferons in anticancer immunity." Nat Rev Immunol. (2015), 15(7):405-14.

\* cited by examiner

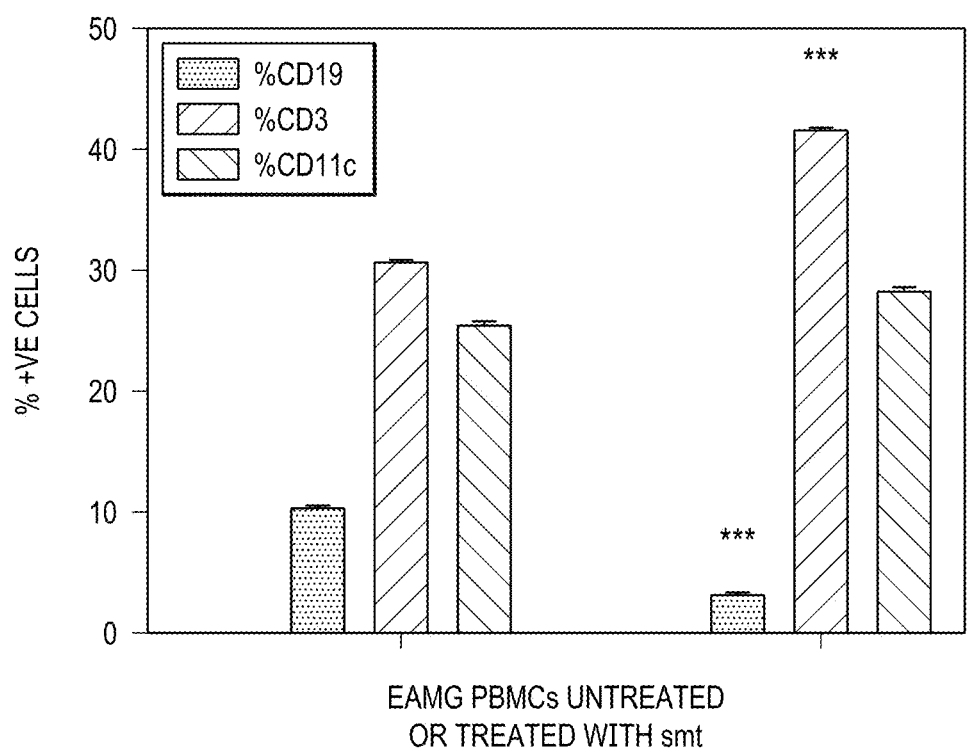

SUSTAINED PRODUCTION OF HIGH AFFINITY ANTIGEN SPECIFIC ANTIBODY BY HIGH DOSE BAFF RECEPTOR-TARGETING MAB-SIRNA CONJUGATE

CROSS-REFERENCE TO RELATED APPLICATIONS

This application claims priority to U.S. Provisional Application Ser. No. 62/446,204, filed Jan. 13, 2017, the entire contents of which are incorporated herein by reference.

STATEMENT OF FEDERALLY FUNDED RESEARCH

None.

TECHNICAL FIELD OF THE INVENTION

The present invention relates in general to the field of generating sustained production of antigen specific antibodies, and more particularly, to a novel therapeutic adjuvant for immune stimulation and uses thereof.

INCORPORATION-BY-REFERENCE OF MATERIALS FILED ON COMPACT DISC

The present application includes a Sequence Listing which has been submitted in ASCII format via EFS-Web and is hereby incorporated by reference in its entirety. Said ASCII copy, created on Jan. 10, 2018, is named UTBM1045_Seq_listing.txt and is 1, KB in size.

BACKGROUND OF THE INVENTION

Without limiting the scope of the invention, its background is described in connection with immune stimulation and enhanced antibody production.

One such technology related to B cells is taught in U.S. Pat. No. 9,006,416, issued to Rossi, et al., and entitled "RNA aptamers against BAFF-R as cell-type specific delivery agents and methods for their use". These inventors teach a B cell specific aptamer-siRNA chimera. The B cell specific aptamer-siRNA chimera may include an RNA aptamer that binds BAFF-R and an siRNA molecule conjugated to the RNA aptamer via a nucleotide linker. In another embodiment, a B cell specific RNA aptamer is provided. The RNA aptamer may be a molecule that binds to BAFF-R that has certain sequences. In some embodiments, the RNA aptamer is conjugated, via a nucleotide linker, to an siRNA molecule that suppresses expression of one or more target oncogenes in one or more B cells. In one aspect, the one or more target oncogenes are selected from Bcl6, Bcl2, STAT3, Cyclin D1, Cyclin E2 and c-myc. In another embodiment, methods for treating a B cell malignancy in a cancer patient are provided. Such methods may include administering a therapeutically effective amount of a therapeutic composition, the therapeutic composition comprising a B cell specific RNA aptamer that binds BAFF-R.

U.S. Pat. No. 8,106,163, issued to Heusser, et al., is entitled "Compositions and methods of use for therapeutic antibodies," and is said to teach antibodies that specifically bind to the BAFF receptor (BAFFR). The invention more specifically relates to specific antibodies that are BAFFR antagonists with in vivo B cell depleting activity and compositions and methods of use for said antibodies to treat pathological disorders that can be treated by killing or depleting B cells, such as systemic lupus erythematosus or rheumatoid arthritis or other autoimmune diseases or lymphomas, leukemias and myelomas.

One such patent application is U.S. Patent Publication No. 20160310590, filed by O'Hagan, et al., entitled "Adjuvant Compositions", which uses adjuvant compositions comprising type 1 interferon inducers, such as double-stranded RNA, in combination with antigen delivery systems and/or immunostimulatory molecules, such as immunostimulatory nucleic acid sequences, for enhancing the immune response of a co-administered antigen, are described.

Another such patent application is U.S. Patent Publication No. 20160279237, filed by Miller, et al. entitled "Adjuvant Compositions and Related Methods", which is said to teach an adjuvant composition that is suited for injectable as well as transdermal administration that generally comprises a lipophile, a polymer of acrylic or methacrylic acid, saline, cholesterol, a saponin, and sodium hydroxide. A vaccine composition is also said to be provided that generally includes the vaccine composition of the lipophile and a DNA component and a method for vaccinating animals and humans utilizing the adjuvant composition of the said disclosure.

SUMMARY OF THE INVENTION

The present invention is construction of a B cell Activating Factor (BAFF)-receptor specific monoclonal antibody and siRNA conjugate that at high dose, triggers sustained production of high level of high affinity antigen specific antibody in vivo in plasma of C57BL1/6J mice. BAFF receptor (BR) specific monoclonal antibody was complexed with a BAFF receptor specific short interfering RNA (siRNA) by the use of linkers and a small protein. A single dose of the complex was administered intraperitoneally in mice at post booster immunization. The mice were previously injected with an immunogen to develop an autoimmune response against a protein antigen. Immediate after one week, unexpectedly, a high titer and high affinity antigen specific antibody spiked in the plasma of mice treated with the conjugate. This antibody production was not transient and the mice continued to produce high affinity and high levels of antibody until 3 months post administration, the experimental end point at which time the mice were euthanized to collect samples for other data collection, as proposed in the funded project.

Further, the mAb-siRNA conjugate is a potent therapeutic adjuvant that boosts production of high level and high affinity vaccine for the treatment of infectious diseases (viral, bacterial and other pathogenic infection) and cancer. Existing technology uses adjuvants that are required to be used at the time of primary immunization. Unlike other adjuvants, the present invention does not need to be co-delivered with the immunogen, but can be used at post immunization and/or when there is a need for sustained production of high level, high affinity antibody. The present invention can also be used in vaccine manufacturing, particularly in an outbreak or the time of vaccine shortage, to boost the production of antibodies and to produce high quality antibody at large amount. Importantly, the immune-stimulatory "high dose" composition can also be used in the treatment of cancer when needed, to target specific receptor of malignant cell if the receptor specific vaccine is used, since the product enhances humoral as well as cellular immunity (T cell stimulation) post vaccination without inducing B cell proliferation, e.g., by enhanced interferon (type 1) producing ability. As used herein, the following amounts are used to differentiate a "low dose" from a "high dose" of the composition. Specifically, a low dose is, e.g., 2 to 6 mg/Kg of total mammal body weight, and can be 2, 4 or 6 mg/Kg. A "high dose", as used herein, is a dose of 10 to 20 mg/Kg of total mammal body weight and can be 10, 15 or 20 mg/Kg body weight. The present invention, therefore, can also be used for producing large-scale antigen specific antibody and type 1 interferons to confer immunological protection of subjects.

The product, mAb conjugate, is not an oil-based bacterial or glycolipid or CpG oligodeoxynucleotide adjuvant but, it includes a bi-specific, protein targeting mAb and mRNA-targeting siRNA which dramatically alters the host immune response. The composition is such that it can be applied to assist a broad range of pathogen specific vaccines. Engineering the mAb and/or siRNA component, the conjugate can also be targeted to any specific pathogenic cell to suppress any target gene expression simultaneously. This synergistic effect, allows for much lower dose of therapeutic vaccine. This product can be used at post immunization as "therapeutic adjuvant" or "therapeutic vaccine" and as and when needed to produce high amount of antigen-specific antibody in vivo in a much shorter time, shorter than in vitro synthetic antibody production time. The other advantage is that this product can replace the need for multiple booster immunizations in order to increase antibody production and thus reduce the cost and time of vaccine production in commercial setting.

In one embodiment, the present invention includes a composition comprising: an anti-BAFF receptor antibody or binding fragment thereof that is bound or conjugated to an siRNA, and shRNA, or both, that targets a BAFF receptor mRNA. In one aspect, the anti-BAFF receptor antibody or binding fragment and the siRNA that targets BAFF receptor mRNA are chemically cross-linked. In another aspect, the composition is formulated in an amount sufficient to be an immune adjuvant. In another aspect, the anti-BAFF receptor antibody or binding fragment and the siRNA that targets BAFF receptor mRNA are chemically cross-linked and a linker is a conditionally self-cleaving RNA sequence, a pH sensitive linker, a hydrophobic sensitive linker, a cleavable linker, a linker that provides a sorting signal, a linker that reduces steric hindrance, a linker that contributes to a condensing ability of the nucleic acid binding domain, a peptide or protein linker, a protamine linker, a polyK linker, or an HIV-TaT protein translocation (TPTV) linker. In another aspect, the anti-BAFF receptor antibody or binding fragment and the siRNA that targets BAFF receptor mRNA are chemically cross-linked and the crosslinker is selected from glutaraldehyde, bissulfosuccinimidyl suberate, carbodiimide, bis(succinimidyl)penta(ethylene glycol), bis(succinimidyl) nona(ethylene glycol), bis(sulfosuccinimidyl) suberate, dimethyl suberimidate, an ethylene glycol characterized by formula $(—CH_2OH—)_n$, wherein n is 2, 3, 4, 5, 6, 7, 8, 9, 10, 11, 12, 13, 14, 15, 16, 17, 18, 19, 20, 21, 22, 23, 24 or 25 and one or both termini of the ethylene glycol are substituted by a succinimide or maleimide group, N-(κ-Maleimidoundecanoyloxy) sulfosuccinimide ester, sulfosuccinimidyl (4-iodoacetyl) aminobenzoate, 1,8-bismaleimidodiethyleneglycol and 1,11-bismaleimidotriethyleneglycol. In another aspect, the composition is adapted for intravenous, intramuscular, oral, parenteral, enteral, intraperitoneal, pulmonary, nasal, subcutaneous, rectal, or transcutaneous administration. In another aspect, the anti-BAFF receptor antibody or B-cell specific protein or binding fragment thereof is attached to a first affinity linker, and a small protein, such as a small basic protein, e.g., protamine, is attached to a second affinity linker, wherein the small protein is capable of binding a BAFF receptor-siRNA or any B-cell specific siRNA. In another aspect, the antibody anti-BAFF receptor antibody or binding fragment thereof is a humanized antibody. In another aspect, the B cell targeting antibody or protein is attached to a small protein by a linker and is optionally conjugated to an siRNA. In another aspect, the BAFF is human BAFF. In another aspect, the composition is provided in a low dose of 2 to 6 mg/Kg of total mammal body weight. In another aspect, the composition is provided in a "high dose", as used herein, is a dose of 10 to 20 mg/Kg of total mammal body weight.

In another embodiment, the present invention includes a method of enhancing an immune response against a target antigen comprising administering to a subject an effective amount of a composition comprising an anti-BAFF receptor antibody or binding fragment thereof that is optionally bound or conjugated to an siRNA that targets BAFF receptor mRNA, wherein the composition is provided before, concurrently with, or after exposing the subject to the target antigen, wherein the composition is an adjuvant to the immunization. In one aspect, the method further comprises the step of optimizing the dose of the composition to significantly increase antibody production against the target antigen by providing a first amount of the composition and after a pre-determined time measuring a first amount of antibody produced, and providing a second amount of the composition having more or less of the composition and measuring after the pre-determined time a second amount of antibody produced, and optionally, adjusting the amount of the composition one or more times until an optimal antibody production is obtained. In another aspect, the target antigen is a cancer antigen. In another aspect, the target antigen is a tumor associated antigen. In another aspect, the target antigen is an infectious disease antigen. In another aspect, the step of exposing the subject to a target antigen is by administering a vaccine/pharmaceutical composition comprising the target antigen. In another aspect, the target antigen is a cancer antigen that is a tumor associated antigen (TAA) is selected from the group consisting of carbonic anhydrase IX, α-fetoprotein (AFP), α-actinin-4, ART-4, B7, Ba 733, BAGE, CA125, CAMEL, CAP-1, CASP-8/m, CCL19, CCL21, CD1, CD1a, CD2, CD3, CD4, CD S, CD8, CD11A, CD14, CD15, CD16, CD18, CD19, CD20, CD21, CD22, CD23, CD25, CD29, CD30, CD32b, CD33, CD37, CD38, CD40, CD40L, CD44, CD45, CD46, CD52, CD54, CD55, CD59, CD64, CD66a-e, CD67, CD70, CD70L, CD74, CD79a, CD80, CD83, CD95, CD126, CD132, CD133, CD138, CD147, CD154, CDC27, CDK-4/m, CDKN2A, CEA, C3, C3a, C3b, C5a, C5, CTLA-4, CXCR4, CXCR7, CXCL12, HIF-1α, colon-specific antigen-p (CSAp), CEA (CEACAM-5), CEACAM-6, c-Met, DAM, EGFR, EGP-1 (TROP-2), EGP-2, ELF2-M, Ep-CAM, fibroblast growth factor (FGF), Flt-1, Flt-3, folate receptor, GAGE-1,2,8, GAGE-3,4,5,6,7; gp100, GRO-β, HLA-DR, human chorionic gonadotropin (HCG), HER2/neu, HMGB-1, hypoxia inducible factor (HIF-1), HSP70-2M, HST-2, Ia, IGF-1R, IFN-γ, IFN-α, IFN-β, IFN-λ1, IFN-λ2, IFN-λ3, IL-4R, IL-6R, IL-13R, IL-15R, IL-17R, IL-18R, IL-2, IL-6, IL-8, IL-12, IL-15, IL-17, IL-18, IL-23, IL-25, insulin-like growth factor-1 (IGF-1), Le-Y, LDR/FUT, macrophage migration inhibitory factor (MIF), MAGE-A1; MAGE-A2; MAGE-A3; MAGE-A4; MAGE-A6; MAGE-A9; MAGE-A10; MAGE-A12; MAGE-C2, MART-1, MART-2, NY-ESO-1, TRAG-3, mCRP, MCP-1, MIP-1A, MIP-1B, MIF, MUC1, MUC2, MUC3, MUC4, MUC5ac, MUC13, MUC16, MUM-1/2, MUM-3, NCA66, NCA95, NCA90, PD-1 receptor, placental growth factor, p53, PLAGL2, prostatic acid phosphatase, PSA, PRAIVIE, PRAME, PSMA, P1GF, ILGF, ILGF-1R, IL-6, IL-25, RS5, RANTES, SAGE, Sp17; SSX-2, SSX-4; survivin, TAC, TAG-72, tenascin, TRAIL receptor, TNF-α, Tn antigen, Thomson-Friedenreich antigens, tumor necrosis antigen, VEGF, ED-B fibronectin, WT-1, an angiogenesis marker, bcl-2, bcl-6, Kras, an oncogene marker, and an oncogene product. In another aspect, the BAFF receptor is human BAFF. In another aspect, the anti-BAFF receptor antibody or binding fragment and the siRNA that targets BAFF receptor mRNA are chemically cross-linked. In another aspect, the method further comprises the step of chemically cross-linking the anti-BAFF receptor antibody or binding fragment and the siRNA that targets BAFF receptor mRNA with a linker that is at least one of: a conditionally self-cleaving RNA sequence, a pH sensitive linker, a hydrophobic sensitive linker, a cleavable linker, a linker that provides a sorting signal, a linker that reduces steric hindrance, a linker that contributes to a condensing ability of the nucleic acid binding domain, a peptide or protein linker, a protamine linker, a polyK linker, or an HIV-TaT protein translocation (TPTV) linker. In another aspect, the method further comprises the step of chemically cross-linking the anti-BAFF receptor antibody or binding fragment and the siRNA that targets BAFF receptor mRNA using one or more of the following cross-linkers: glutaraldehyde, bissulfosuccinimidyl suberate, carbodiimide, bis(succinimidyl)penta(ethylene glycol), bis(succinimidyl) nona(ethylene glycol), bis(sulfosuccinimidyl) suberate, dimethyl suberimidate, an ethylene glycol characterized by formula (—CH$_2$OH—)$_n$, wherein n is 2, 3, 4, 5, 6, 7, 8, 9, 10, 11, 12, 13, 14, 15, 16, 17, 18, 19, 20, 21, 22, 23, 24 or 25 and one or both termini of the ethylene glycol are substituted by a succinimide or maleimide group, N-(κ-Maleimidoundecanoyloxy) sulfosuccinimide ester, sulfosuccinimidyl (4-iodoacetyl) aminobenzoate, 1,8-bismaleimidodiethyleneglycol, or 1,11-bismaleimidotriethyleneglycol. In another aspect, the method further comprises the step of adapting the composition for intravenous, intramuscular, oral, parenteral, enteral, intraperitoneal, pulmonary, nasal, subcutaneous, rectal, or transcutaneous administration. In another aspect, wherein the anti-BAFF receptor antibody or binding fragment thereof and the siRNA, an shRNA, or both are conjugated with a small basic protein. In another aspect, the small basic protein is protamine. In another aspect, the anti-BAFF receptor antibody or binding fragment thereof is attached to a first affinity linker, and a is attached to a second affinity linker, wherein the protamine is capable of binding a BAFF receptor-siRNA. In another aspect, the composition is provided in an amount sufficient to deplete BAFF receptor in at least one of peripheral blood mononuclear cells, lymph node cells, or splenocytes. In another aspect, the composition is provided in a low dose of 2 to 6 mg/Kg of total mammal body weight. In another aspect, the composition is provided in a "high dose", as used herein, is a dose of 10 to 20 mg/Kg of total mammal body weight.

Yet another embodiment of the present invention includes a method of treating or preventing myasthenia gravis comprising administering to a subject in need thereof a therapeutically or prophylactically effective amount of a composition comprising an anti-BAFF receptor antibody or binding fragment thereof that is bound or conjugated to an siRNA that targets BAFF receptor mRNA. In another aspect, the BAFF receptor is a human BAFF receptor. In another aspect, the method further comprises the step of optimizing the dose of the composition to reduce or eliminate the symptoms of myasthenia gravis in a human or an animal. In another aspect, the method further comprises the step of optimizing the dose of the composition to not significantly reduce serum autoantibody or IFNγ level. In another aspect, the method further comprises the step of optimizing the dose of the composition to induce significantly higher IL4 and IL10 levels.

In yet another embodiment, the present invention includes a method of evaluating an adjuvant, the method comprising: a) measuring at least one of antibodies from a blood sample obtained from a subject from a set of patients; b) administering the adjuvant comprising an affinity linkers and protamine modified anti-BAFF receptor antibody or binding fragment thereof that is bound or optionally conjugated to an siRNA, or shRNA, or both, that targets a BAFF receptor mRNA to a first subset of the patients, and a placebo to a second subset of the patients; c) repeating step a) after the administration of the adjuvant or the placebo; and d) determining if the adjuvant increases the levels of antibodies in the blood sample that is statistically significant as compared to any reduction occurring in the second subset of patients, wherein a statistically significant change indicates that the adjuvant is useful to increase antibody production. In another aspect, the method further comprises the step of optimizing the dose of the composition to significantly increase antibody production against the target antigen. In another aspect, the target antigen is a cancer antigen that is a tumor associated antigen selected from the group consisting of carbonic anhydrase IX, α-fetoprotein (AFP), α-actinin-4, ART-4, B7, Ba 733, BAGE, CA125, CAMEL, CAP-1, CASP-8/m, CCL19, CCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD44, CD45, CD46, CD52, CD54, CD55, CD59, CD64, CD66a-e, CD67, CD70, CD70L, CD74, CD79a, CD80, CD83, CD95, CD126, CD132, CD133, CD138, CD147, CD154, CDC27, CDK-4/m, CDKN2A, CEA, C3, C3a, C3b, C5a, C5, CTLA-4, CXCR4, CXCR7, CXCL12, HIF-1α, colon-specific antigen-p (CSAp), CEA (CEACAM-5), CEACAM-6, c-Met, DAM, EGFR, EGP-1 (TROP-2), EGP-2, ELF2-M, Ep-CAM, fibroblast growth factor (FGF), Flt-1, Flt-3, folate receptor, GAGE-1,2,8, GAGE-3,4,5,6,7; gp100, GRO-β, HLA-DR, human chorionic gonadotropin (HCG), HER2/neu, HMGB-1, hypoxia inducible factor (HIF-1), HSP70-2M, HST-2, Ia, IGF-1R, IFN-γ, IFN-α, IFN-β, IFN-λ1, IFN-λ2, IFN-λ3, IL-4R, IL-6R, IL-13R, IL-15R, IL-17R, IL-18R, IL-2, IL-6, IL-8, IL-12, IL-15, IL-17, IL-18, IL-23, IL-25, insulin-like growth factor-1 (IGF-1), Le-Y, LDR/FUT, macrophage migration inhibitory factor (MIF), MAGE-A1; MAGE-A2; MAGE-A3; MAGE-A4; MAGE-A6; MAGE-A9; MAGE-A10; MAGE-A12; MAGE-C2, MART-1, MART-2, NY-ESO-1, TRAG-3, mCRP, MCP-1, MIP-1A, MIP-1B, MIF, MUC1, MUC2, MUC3, MUC4, MUC5ac, MUC13, MUC16, MUM-1/2, MUM-3, NCA66, NCA95, NCA90, PD-1 receptor, placental growth factor, p53, PLAGL2, prostatic acid phosphatase, PSA, PRAIVIE, PRAME, PSMA, P1GF, ILGF, ILGF-1R, IL-6, IL-25, RS5, RANTES, SAGE, Sp17; SSX-2, SSX-4; survivin, TAC, TAG-72, tenascin, TRAIL receptor, TNF-α, Tn antigen, Thomson-Friedenreich antigens, tumor necrosis antigen, VEGF, ED-B fibronectin, WT-1, an angiogenesis marker, bcl-2, bcl-6, Kras, an oncogene marker, and an oncogene product.

In yet another embodiment, the present invention includes a method of evaluating a candidate drug believed to be useful at low dose in treating an autoimmune disease, the method comprising: a) measuring at least one of autoantibody, IFNγ level, IL4 or IL10 levels from a blood sample or lymph node tissue obtained from a subject having the autoimmune disease from a set of patients; b) administering a candidate drug comprising an anti-BAFF receptor antibody or binding fragment or other B cell targeting protein or antibody thereof that is optionally bound or conjugated to an siRNA, and shRNA, or both, that targets a BAFF receptor mRNA or other B cell specific mRNA to a first subset of the patients, and a placebo to a second subset of the patients; c) repeating step a) after the administration of the candidate drug or the placebo; d) determining if the candidate drug reduces levels of autoantibody or IFNγ level, or increases the IL4 or IL10 levels that is statistically significant as compared to any reduction occurring in the second subset of patients, wherein a statistically significant change indicates that the candidate drug is useful in treating the autoimmune disease; and the autoimmune disease; and e) determining if the candidate drug increases levels of antigen specific antibody or type 1 IFN levels that is statistically significant as compared to increase in control subset of patients, wherein a statistically significant change indicates that the candidate is useful as an antimicrobial and anti-cancer immunomodulator or vaccine adjuvant. In another aspect, the composition is provided in a low dose of 2 to 6 mg/Kg of total mammal body weight. In another aspect, the composition is provided in a "high dose", as used herein, is a dose of 10 to 20 mg/Kg of total mammal body weight. In another aspect, the method further comprises the step of raising or lowering the dose of the candidate drug to optimize the treatment of the autoimmune disease. In another aspect, the autoimmune disease is myasthenia gravis.

BRIEF DESCRIPTION OF THE DRAWINGS

For a more complete understanding of the features and advantages of the present invention, reference is now made to the detailed description of the invention along with the accompanying figures and in which:

FIG. 1A is a diagram showing preparation of conjugate for targeted delivery. FIG. 1B shows rat antimouse mAb (BAFF receptor-specific) and a bovine IgG control were coupled to linkers and protamines and then conjugated with siRNAs specific for BAFF receptor and GAPDH. Purified conjugates were electrophoresed in 20% native polyacrylamide gel. The doublets on lanes 2 and 4 represent upward shifting of higher molecular-weight conjugates from unreacted, residual siRNAs (more prominent due to separation on lane 4) and unconjugated siRNA controls (lanes 1 and 3). The gel was de-stained and then re-stained in Coomassie blue (bottom panel) to show antibody component of the conjugate. FIG. 1C shows the stability of conjugate at 4° C. (decreases with time, about ⅓ amount remains after 24 h as shown in lane 4, bottom panel). Unconjugated, protamine bound mAb (mt), due to the high molecular mass, fails to penetrate the gel and therefore remains trapped in the well. Coomassie blue stained gel showing mAb-siRNA conjugates. MW, molecular weight marker. FIGS. 1B and 1C show representative results from 3 independent experiments.

FIG. 2A shows internalization of BAFF receptor specific mAb-siRNA conjugate in GFP and BAFF receptor coexpressing rat myeloma Y3 cells. These cells were incubated for 24 h with conjugates consisted of BAFF receptor specific mAb and Cy-3 labeled nonspecific siRNA. Cells were then treated with chymotrypsin in PBS to remove any membrane bound fluorescence, counter-stained with Hoechst nuclear stain, washed, cytospun and observed under fluorescence Olympus microscope. Shown in top panel is a selective zone in the slide with Y3 cells, emitting green fluorescence, nuclear blue-Hoechst stain indicating live cells (middle), cells positive for Cy3+ red fluorescence (with central greyish nuclei) due to internalized mAb-siRNA conjugates and an overlay of 3 colors showing presence of cytosolic Cy3-containing conjugates surrounding the nucleus in each cell. FIG. 2B shows B cells, magnetically purified from PBMCs of EAMG mice were plated in DMEM and 5% Fetal Bovine Serum and spin-transfected with fluorescein labeled non-specific siRNA conjugated to BAFF receptor specific mAb. After 24 h, cells were protease (chymotrypsin) treated, washed, cytospun and immediately observed under fluorescence Olympus microscope. The result in the left panel shows an abundance of B cells, emitting green fluorescence due to internalized mAb-siRNA conjugates that contained fluorescein labeled siRNA. Each result (FIG. 2A and FIG. 2B) is a representative of 3 independent experiments.

FIG. 3A shows GFP-BAFF receptor coexpressing Y3 cells were incubated either with BAFF receptor specific conjugate, protamine unconjugated mAb-siRNA, IgG-siRNA, IgG—only controls for 48 hours. Flow cytometry showing levels of BAFF receptor reduction in live cells treated or untreated with conjugate. This experiment is a representative of 3 independent experiments. In all 3 experiments, BAFF receptor conjugate (smt) significantly reduced BAFF receptor expression compared to respective controls. The bar graph on right panel shows mean fluorescent intensity (MFI) of GFP. FIG. 3B shows that for in vivo dose kinetics, EAMG mice treated with conjugates were bled from tail vein at 2 weeks post treatment and assessed suppression of BAFF receptor in PBMCs by flow analysis. smt1, high dose (350 μg per 25 g), smt2 (125 μg per 25 g) and smt3 (50 μg per 25 g), low doses. FIG. 3C are representative images showing presence of propidium iodide (red fluorescence) positive Y3 cells treated with BAFF receptor specific conjugates as compared to untreated cells (GFP+).

FIGS. 4A to 4E show conjugate mediated reduction of BAFF receptor, B cell antigens and expression of Fas in vivo in EAMG mice. FIG. 4A shows real-time PCR of purified PBMCs from EAMG mice at 8 weeks post treatment, that demonstrates the effect of conjugate treatment on relative mRNA levels of BAFF receptor (CD268), CD19 as well as the complement receptor (CR)-2. Fold changes≅ΔΔCT relative to β actin and untreated controls. The result is a representative of 3 independent experiments, n=6 per group of mice. Values were normalized to the expression of β actin in the same sample at the same time. FIG. 4B shows flow cytometry analyzed frequencies of BAFF receptor +CD19+ and BAFF receptor +B220+ cells and Fas expression in those cells in lymph nodes and spleen of conjugate treated mice. EAMG mice treated with conjugates were euthanized at 9 weeks post treatment. Splenocytes and lymph node cells were isolated and stained for cell phenotyping using Abs conjugated to fluorescent markers. FIG. 4C shows representative flow cytometry data (2 experiments) showing frequency of BAFF receptor (CD268), CD19 and B220 cell population in lymph node (inguinal) and spleen. FIG. 4D shows representative data showing the percentages of cells positive for GL7. FIG. 4E is a graph that shows the percent positive cells for CD3, CD11c or CD19.

FIG. 5A shows grip strength. Groups of EAMG mice with established disease (post $2^{nd}$ booster immunization) were treated i.p. with BAFF receptor specific conjugate or unconjugated other controls, once a week for 3 weeks. Forelimb grip strength of mice was measured once weekly on a grip meter prior to treatment and 4 times (weeks 3, 4, 7, 9) post treatment. Grip strength value of each mouse shown above (n=6 per group) was the mean of 5 repeats. FIG. 5B shows body weight. Body weights (g) of untreated and conjugate treated mice were taken prior to sacrifice on $9^{th}$ week and potted as shown.

FIG. 6A shows serum levels of anti-AChR Ab was determined by ELISA using affinity-purified mouse AChR as a coating antigen. The results are the representatives of 3 independent experiments. Similar results were obtained by using serum from mice bled at 3 different post treatment times (weeks 2, 4, 6, 9). FIG. 6B shows antibody affinity, as determined by radioimmunoassay by precipitating anti-AChR Ab from experimental mouse serum (prior to euthanasia) with $^{125}$I labeled Bungarotoxin labeled normal mouse AChR (n=4 per group, for this experiment).

FIG. 7A shows R-PCR representing relative mRNA fold changes of IFNα/β mRNAs in PBMCs, LN and spleen of EAMG mice treated or not with conjugates. Relative mRNA levels were determined by normalization of gene expressions with that of β actin. FIG. 7B shows serum from EAMG mice, bled from tail vein at 8 weeks post treatment, was used for cytokine ELISA. Serum levels of IFNγ, IL6, IL4, and IL10 were measured by using appropriate, commercial ELISA kits (EBIOSCIENCE®). Representative histogram indicates cytokine levels. Each experiment was repeated 3 times.

DETAILED DESCRIPTION OF THE INVENTION

Figure 1A:
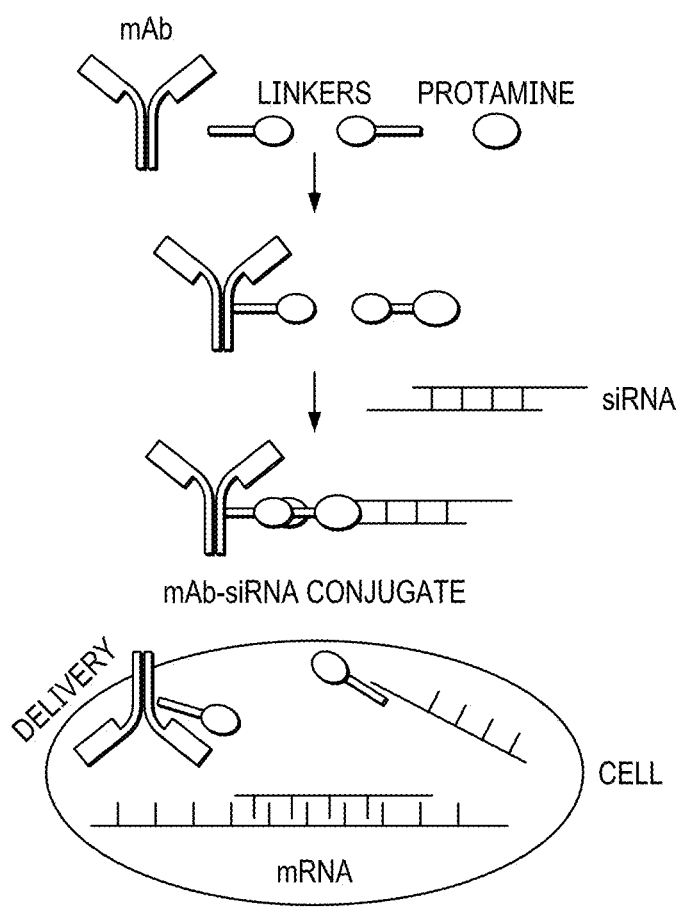
FIGS. 1A to 1C show the verification of mAb-siRNA conjugates (smt).

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention.

As used herein, the term "antibody", "immunoglobulin", and "antibody/immunoglobulin binding fragments" refers to polyclonal and monoclonal antibody preparations, as well as preparations including hybrid antibodies, altered antibodies, F(ab')2 fragments, F(ab) fragments, Fv fragments, single domain antibodies, chimeric antibodies, humanized antibodies, and functional fragments or a protein thereof that exhibit immunological binding properties of the antibody molecule against a specific antigenic target.

As used herein, the term "antigen-binding site" or "binding portion" refers to the part of the antibody or immunoglobulin molecule that participates in specific antigen binding. The antigen-binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

As used herein, the term "adjuvant" refers to a substance that non-specifically changes or enhances an antigen-specific immune response of an organism to the antigen. Generally, adjuvants are non-toxic, have high-purity, are degradable, and are stable. The recombinant adjuvant of the present invention meets all of these requirements; it is non-toxic, highly-pure, degradable, and stable. Adjuvants are often included as one component in a vaccine or therapeutic composition that increases the specific immune response to the antigen. However, the present invention includes a novel adjuvant that does not have to be concurrently administered with the antigen to enhance an immune response, e.g., a humoral immune response. Unlike the common principle of action of other immunologic adjuvants, such as: (1) increasing surface area of an antigen to improve the immunogenicity thereof; (2) causing slow-release of the antigen to extend the retention time of the antigen in tissue; or (3) promoting an inflammatory reaction to stimulate active immune response, the present invention targets the B cells directly to enhance the production of antigen specific antibodies and type 1 interferons.

As used herein, the term "BAFF receptor" refers to BAFF receptor (B-cell activating factor receptor, BAFF-R, BR, CD268), also known as tumor necrosis factor receptor superfamily member 13C (TNFRSF13C), which is a membrane protein of the TNF receptor superfamily, which recognizes BAFF. In humans, the BAFF receptor is encoded by the TNFRSF13C gene (UniProt Q96RJ3, GenBank AF373846.1); relevant sequences incorporated herein by reference.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, F(ab')$_2$, Fv, and other fragments that exhibit immunological binding properties of the parent monoclonal antibody molecule.

As used herein, the term "myasthenia gravis" refers to any chronic progressive muscular weakness. Generally, myasthenia gravis commonly affects muscles of the eyes, face, and swallowing, but can also result in double vision, drooping eyelids, trouble talking, and trouble walking. Myasthenia gravis is an autoimmune disease that results from antibodies that block nicotinic acetylcholine receptors at the junction between the nerve and muscle, which prevents nerve impulses from triggering muscle contractions.

Synthesis techniques for the preparation of suitable peptide/protein-RNA linker molecules are conventional, and any of the techniques listed below may be employed in the context of the present invention, such as those described in WO2009083738, relevant portions incorporated herein by reference. Incorporation by reference herein is made to the following U.S. patents: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having lactam backbones; U.S. Pat. No. 5,571,902, drawn to methods and materials for the synthesis of oligonucleotides; U.S. Pat. No. 5,578,718, drawn to nucleosides having alkylthio-groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopuhne compounds; U.S. Pat. No. 5,587,469, drawn to oligonucleotides having N-2 substituted purines; U.S. Pat. No. 5,587,470, drawn to oligonucleotides having 3-deazapurines; U.S. Pat. Nos. 5,223,168, and 5,608,046, both drawn to conjugated 4'-desmethyl nucleoside analogs; U.S. Pat. Nos. 5,602,240, and 5,610,289, drawn to backbone-modified oligonucleotide analogs; U.S. Pat. Nos. 6,262,241, and 5,459,255, drawn to, inter alia, methods of synthesizing 2'-fluoro-oligonucleotides. Each of these publications is hereby incorporated in its entirety by reference thereto.

Many different linkers can be used with the present invention. In the present invention, linkers were used to associate a protamine or a small protein with BAFF receptor-specific mAb. In one non-limiting example, a protamine linker (also referred to herein as a coupling reagent) can be used. A protamine linker generally comprises amino acids 8-29 of protamine, namely RSQSRSRYYRQRQRSRRR-RRRS (SEQ ID NO: 1). Other protamine sequences (e.g. a peptide comprising at least amino acids 12-20, at least amino acids 10-24, or at least amino acids 10-26 of protamine) are equally suitable. The linker can be incorporated at the N- or C-terminus of the translocation component, or within a surface exposed loop region of translocation component. In another example, a polylysine linker (also known as polyK linker) is used. One polyK linker comprises 5-30 or 5-20 or 5-15 or 7-10 lysine residues, optionally including one or more (but preferably no more than 5) non-lysine residues. The linker can be incorporated at the N- or C-terminus of the translocation component, or within a surface exposed loop region of translocation component. In another example, a TPTV linker (also known as a HIV-TaT protein translocation domain linker) can be used. One such TPTV linker comprises residues 47-57 of HIV-TAT. TPTV linkers typically comprise 5-30 or 5-20 or 5-15 or 7-10 amino acid residues. The linker can be incorporated at the N- or C-terminus of the translocation component, or within a surface exposed loop region of translocation component.

In some embodiments, the anti-BAFF receptor antibody or binding fragment thereof is conjugated to the nucleic acid active agent, e.g., RNAi agent or miRNA agent using a protamine linker, as disclosed in the U.S. Patent Application Publication Nos. US2002/0132990 and US2004/0023902, which are incorporated herein in their entirety by reference. In particular, where a protamine or protamine like agent, the methods, reagents and reference that describe the preparation of protamine associated with the present product, anti-BAFF receptor antibody or binding fragment thereof are disclosed in U.S. Pat. Applications US2007/012152, and US2010/0209440, which are each incorporated herein in their entirety by reference. In some embodiments, a protamine linker encompassed for use in the present invention comprises SEQ ID NO: 1-6 disclosed in US 2010/0209440.

Acid cleavable linkers can also be used with the present invention and include, but are not limited to, bismaleimideothoxy propane, adipic acid dihydrazide linkers (see, e.g., Fattom et al., Infection & Immun. 60:584 589, 1992) and acid labile transferrin conjugates that contain a sufficient portion of transferrin to permit entry into the intracellular transferrin cycling pathway (see, e.g., Welhoner et al., J. Biol. Chem. 266:4309 4314, 1991). Conjugates linked via acid cleavable linkers should be preferentially cleaved in acidic intracellular compartments, such as the endosome.

Photocleavable linkers can also be used with the present invention. Photocleavable linkers are cleaved upon exposure to light (see, e.g., Goldmacher et al., Bioconj. Chem. 3:104 107, 1992), thereby releasing the targeted agent upon exposure to light. (Hazum et al., Proc. Eur. Pept. Symp., 16th, Brunfeldt, K (Ed), pp. 105 110, 1981; nitrobenzyl group as a photocleavable protective group for cysteine; Yen et al., Makromol. Chem 190:69 82, 1989; water soluble photocleavable copolymers, including hydroxypropylmethacrylamide copolymer, glycine copolymer, fluorescein copolymer and methylrhodamine copolymer; and Senter et al., Photochem. Photobiol. 42:231 237, 1985; nitrobenzyloxycarbonyl chloride cross linking reagents that produce photocleavable linkages), relevant portions incorporated herein by reference. Such linkers are particularly useful in treating dermatological or ophthalmic conditions. In addition, other tissues, such as blood vessels that can be exposed to light using fiber-optics during angioplasty in the prevention or treatment of restenosis may benefit from the use of photocleavable linkers. After administration of the conjugate, the eye or skin or other body part is exposed to light, resulting in release of the targeted moiety from the conjugate. Heat sensitive linkers would also have similar applicability.

In one example, the protamine and linker modified BAFF receptor-specific antibody yields high quantity of host-produced antigen specific antibody. In another embodiment, the protamine and linker modified BAFF receptor-specific antibody conjugated to BAFF receptor-specific siRNA yields host-product antigen specific antibody with enhanced antigen specificity. In certain embodiments, the composition of the present invention can also be used as an adjuvant in immune therapy. It was found that a high dose of the composition led to significant antigen dependent increases in circulating antibodies. Thus, the present invention can be used to target specific antigens, such as cancer antigens, Tumor Associated Antigens (TAA), or infectious disease antigens, e.g., antigens found on bacteria, viruses, fungi, helminths, protozoans, or insects. For example, the protamine and linker modified BAFF receptor-specific antibody can be conjugated to a TAA-specific siRNA. Tumor associated antigens (TAA) are often classified into four main groups based on their expression and tissue distribution, and these include the following: (1) antigens unique to a tumor; (2) shared lineage restricted antigens; (3) shared tumor-specific antigens; and (4) shared tumor-specific TAAs.

Surprisingly, the composition of the present invention has been found to lead to different immune responses based on the amount of dose provided to the subject. As used herein, the following amounts are used to differentiate a "low dose" from a "high dose" of the composition. Specifically, a low dose is, e.g., 2 to 6 mg/Kg of total mammal body weight, and can be 2, 4 or 6 mg/Kg. A "high dose", as used herein, is a dose of 10 to 20 mg/Kg of total mammal body weight and can be 10, 15 or 20 mg/Kg.

Unique antigens result from single mutations that are tumor- and patient-specific and therefore are only expressed in neoplastic cells (e.g., MUM1). Unique antigens are often considered ideal for immunotherapy since tumor cells can be specifically targeted without destroying nearby normal tissue and they may be relatively strong antigens. However, because they are also usually patient-specific, the identification of the mutated gene and then the generation of an individualized CTL product targeting the identified antigen is highly labor and cost intensive.

The shared lineage-restricted antigens, expressed on melanoma cells as well as their normal tissue of origin, e.g., MART, gp100, or Melan-A. Shared lineage-restricted antigens are also strongly immunostimulatory, equivalent almost to weak viral antigens, enabling the efficient and relatively simple generation and expansion of tumor-specific T cells from healthy donors and patients with minimal in vitro manipulation.

Shared tumor-specific TAA (e.g., the cancer testis antigens (CTA), MAGE, BAGE, GAGE, NY-ESO-1, SSX, and PRAME) are expressed in multiple tumors but not in healthy organs, with the exception of germ line tissues that are immune privileged and therefore not susceptible to T cell attack. CTAs are optimal targets for CTLs, since these can be produced on a large scale to provide broad-spectrum protection against a variety of tumors. CTAs have been targeted in both vaccine and T cell therapy protocols, with evidence of clinical efficacy. The latter group of antigens are overexpressed in many different tumors but expressed at low levels in healthy tissue (e.g. hTERT, CEA and Survivin). T cells targeted to these antigens carry the risk of inducing some collateral damage to normal tissues co-expressing the antigen (e.g. CEA and normal biliary epithelium), and there is limited clinical data available regarding the safety of targeting these antigens in vivo. However, Survivin- and CEA-specific T cells have been isolated from the peripheral blood of patients who have cleared their tumors, and increases in Survivin-specific T cells in patients receiving oncolytic viruses have been reported suggesting that they can have efficacy without toxicity in patients. A non-limiting list of cancer antigens includes: carbonic anhydrase IX, α-fetoprotein (AFP), α-actinin-4, ART-4, B7, Ba 733, BAGE, CA125, CAMEL, CAP-1, CASP-8/m, CCL19, CCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD44, CD45, CD46, CD52, CD54, CD55, CD59, CD64, CD66a-e, CD67, CD70, CD70L, CD74, CD79a, CD80, CD83, CD95, CD126, CD132, CD133, CD138, CD147, CD154, CDC27, CDK-4/m, CDKN2A, CEA, C3, C3a, C3b, C5a, C5, CTLA-4, CXCR4, CXCR7, CXCL12, HIF-1α, colon-specific antigen-p (CSAp), CEA (CEACAM-5), CEACAM-6, c-Met, DAM, EGFR, EGP-1 (TROP-2), EGP-2, ELF2-M, Ep-CAM, fibroblast growth factor (FGF), Flt-1, Flt-3, folate receptor, GAGE-1,2,8, GAGE-3,4,5,6,7; gp100, GRO-β, HLA-DR, human chorionic gonadotropin (HCG), HER2/neu, HMGB-1, hypoxia inducible factor (HIF-1), HSP70-2M, HST-2, Ia, IGF-1R, IFN-γ, IFN-α, IFN-β, IFN-λ1, IFN-λ2, IFN-λ3, IL-4R, IL-6R, IL-13R, IL-15R, IL-17R, IL-18R, IL-2, IL-6, IL-8, IL-12, IL-15, IL-17, IL-18, IL-23, IL-25, insulin-like growth factor-1 (IGF-1), Le-Y, LDR/FUT, macrophage migration inhibitory factor (MIF), MAGE-A1; MAGE-A2; MAGE-A3; MAGE-A4; MAGE-A6; MAGE-A9; MAGE-A10; MAGE-A12; MAGE-C2, MART-1, MART-2, NY-ESO-1, TRAG-3, mCRP, MCP-1, MIP-1A, MIP-1B, MIF, MUC1, MUC2, MUC3, MUC4, MUC5ac, MUC13, MUC16, MUM-1/2, MUM-3, NCA66, NCA95, NCA90, PD-1 receptor, placental growth factor, p53, PLAGL2, prostatic acid phosphatase, PSA, PRAIVIE, PRAME, PSMA, P1GF, ILGF, ILGF-1R, IL-6, IL-25, RS5, RANTES, SAGE, Sp17; SSX-2, SSX-4; survivin, TAC, TAG-72, tenascin, TRAIL receptor, TNF-α, Tn antigen, Thomson-Friedenreich antigens, tumor necrosis antigen, VEGF, ED-B fibronectin, WT-1, an angiogenesis marker, bcl-2, bcl-6, Kras, an oncogene marker, and oncogene products.

The inventors investigated the therapeutic effects of a conjugate of BAFF receptor specific monoclonal antibody and short interference RNA in a mouse model of myasthenia gravis (EAMG). Whereas high-dose siRNA conjugate resulted in significant accumulation of Fas expressing CD19+/B220+ cells and concurrent expression of type 1 interferon in lymph nodes, low-dose conjugate did not induce FAS expression but caused marked BAFF receptor deficiency in lymph nodes and reduced levels of Th2 cytokines that possibly led to improved MG symptoms. Unexpectedly, despite inhibiting BAFF receptor significantly in PBMCs and secondary lymphoid organs, conjugate treatment did not reduce the levels of autoantibody. Rather, at high dose, it caused robust increase in high affinity anti-AChR antibody and increased levels of serum IL10 and IL-4 cytokines. These findings reveal a previously undocumented, dose dependent, immunomodulatory distant effect resulting from BAFF receptor specific mAb-siRNA conjugate treatment in an in vivo model of autoimmune disease.

Myasthenia gravis (MG) is an under-diagnosed autoimmune disease that impairs muscle strength of the eyelids, tongue, and even the limbs. The cause is an autoantibody- and complement-mediated destruction of acetylcholine receptors (AChR) at the neuromuscular junction. Ninety percent of patients with acquired generalized MG have circulating anti-AChR autoantibody [1]. Current therapies for myasthenia are primarily steroids, immunosuppressive therapies and plasmapheresis, which have many side effects including global immune suppression, infections and hypertension. Thus, there is an increasing need for new and improved therapy for MG. For use with the present invention, animal model of MG can be used as a model system for antigenic stimulation of the immune system.

siRNA therapy is an attractive treatment approach for many diseases because of its strong target specificity, short in vivo persistence and rapid serum clearance. Therapeutic siRNAs are cost effective and can be made more quickly and efficiently compared to small molecule peptides or inhibitor. They are also useful to inhibit protein that does not have a binding pocket for the inhibitors. The main challenge of siRNA-only therapy is achieving efficient target cell or tissue-restricted delivery to a particular cell or tissue site critical to suppression of pathogenic responses. Although mAb can be utilized to produce cell-specific effects, mAb-only therapy is limited by the non-specificity and toxicity at high therapeutic doses, which after prolonged use can cause adverse immune-complex on serum components and kidney [2].

The present inventors developed a novel mAb-siRNA conjugate that inhibits the target gene in a target pathogenic cell, as a result of the highly-specific target cell recognition properties of a receptor-specific mAb and the specificity of a gene specific siRNA for a target mRNA. Studies have demonstrated a safe and target-specific delivery of Ab-siRNA conjugate. The present invention is a novel, B cell specific mAb-siRNA conjugate molecule tested in a mouse model of MG, experimental autoimmune MG or EAMG for a cell specific MG therapy.

MG is a T cell dependent and B cell mediated autoimmune disease. Importantly, pathogenesis of MG is associated with up-regulated expression or hyper-activation of many immune response genes, which include some cell surface receptors that are preferentially expressed in specific immune cells. Among those are certain B cell-specific receptors that critically contribute to the survival, pathogenic development, and differentiation of B cells that mediate the autoimmune manifestation of MG. As shown herein, silencing the expression of specific genes solely in these activated B cells and depleting those cells by bi-specific action of a mAb-siRNA conjugate interrupts the pathogenesis of EAMG without exerting a nonspecific target effects. In this study, therapeutic responses of a mAb-siRNA conjugate designed to target a receptor in pathogenic mature B cells in EAMG mice were demonstrated. The BAFF Receptor (TNF receptor superfamily member 13c, TNFRF13c; CD268), is indispensable for the maintenance of all mature B cells (the precursor plasma cells) and CD19+CD27+ memory cells [6, 7]. BAFF receptor, predominantly expressed on mature and activated B cells in EAMG and also in MG, responds to its ligand BAFF to elicit NF-kB-mediated survival signals in those cells [8]. BAFF receptor, but not BAFF, is a suitable therapeutic target for mAb-siRNA conjugate, as BAFF is expressed in a variety of cells, including non-pathogenic epithelial and neuronal cells. BAFF receptor mutant mice have reduced numbers of peripheral B cells and circulating immunoglobulin, and their lymph nodes lack germinal follicles and marginal zones [9]. Therefore, the inventors targeted these cells with a BAFF receptor specific mAb-siRNA conjugate to prevent their further differentiation into pathogenic autoantibody producing plasma cells.

siRNAs and mAb. The pre-designed, validated and in vivo grade (HPLC-purified) BAFF receptor or TNFRSF13c (NM_028075.2), and a corresponding non-targeting siRNA were purchased from Life Technologies (Carlsbad, Calif.). Rat anti-mouse mAbs for BAFF receptor were purchased from Novus Biologicals (Littleton, Colo.) and LS Bioscience (Seattle, Wash.). Cy-tagged and fluorescein labeled non-targeting siRNAs were purchased from Cell Signaling (Beverly, Mass.) and Thermo Fisher (Waltham, Mass.), respectively. For flow cytometry, antibodies labeled with PE, PerCP, FITC, Alexa etc. were purchased from BD Bioscience (San Jose, Calif.), Biolegend (San Diego, Calif.) and eBioscience (San Diego, Calif.).

Conjugation of mAb and siRNA. Reagents for conjugation were purchased from Sigma (MO), Bioo Scientific (Austin, Tex.), and Abcam (Cambridge, Mass.). The concentrated and buffer-exchanged mAb @3 µg/µl (5 mg total) was first coupled to Protamine by a bivalent cross linker in the presence of a modification/conjugation buffer containing Di-Methyl Formamide. Protamine coupled modified mAb (mt) was purified on PD-10 desalting column purchased from GE (Pittsburgh, Pa.), concentrated and then quantified [11]. Mt was then conjugated with a BAFF receptor specific duplex siRNA (~19 nucleotides) at 1:1 by electrostatic reaction. Unreacted molecules (mt and siRNA) were removed by column purification (Abcam, MA). Two µg of purified conjugates (BAFF receptor-specific) and a conjugate of bovine IgG control and GAPDH specific siRNA were electrophoresed in a 20% polyacrylamide gel. Efficiency of conjugate formation and conjugate stability were verified by electrophoresis in 20% native, polyacrylamide gel stained with ethidium bromide and Coomassie blue.

Cell Line and Mouse Model of MG.

Y3 rat myeloma B cells, having bicistronic expression of BAFF receptor and GFP, were plated at 20,000 cells per mL of DMEM and 5% FBS. BAFF receptor specific mAb-siRNA conjugate (composed of mAb at 1 µg and siRNA at 3 µg) per well was added and incubated for 24 h or 48 hours depending on the need for experiments. Cells were washed and stained appropriately either to measure GFP fluorescence by flow cytometry or to observe GFP fluorescence by immunocytochemistry.

C57BL/6 mice were immunized with Torpedo AChR (20 µg each) in complete Freund's adjuvant (CFA), and boosted twice to induce the disease. Grade 2 or 3 MG disease in immunized mice (as assessed by a blinded observation) were confirmed by a weaker grip of limb muscle recorded from a digital Dynamometer (Chatillion Digital Force Gauge, Columbus Instruments, OH), hunchback posture, restricted mobility, and elevated anti-AChR Ab in serum compared to CFA only controls [12]. All mice were purchased from Jackson Lab (Bar Harbor, Me.) were housed and maintained in a barrier facility as per the NIH and UTMB Animal Care and Use Committee guidelines.

Internalization of BAFF receptor-specific conjugate in cell. Rat myeloma Y3 B cells, stably transduced with bicistronic retrovirus for GFP-BAFF receptor coexpression, were similarly incubated with conjugates of BAFF receptor mAb and Cy-3 labeled siRNA. After 24 h, cells were protease treated for 5 min to remove surface fluorescence, washed, cytospun, and immediately observed under fluorescence Olympus microscope to detect intracellular fluorescence from internalized conjugates.

C57BL/6 EAMG mice were bled from the tail vein. PBMCs were isolated by using Lymphoprep (Stemcell Technologies, Cambridge, Mass.). CD19+B cells were purified from PBMCs by using EasySep magnetic B cell isolation kit (Stemcell Technologies). B cells were washed and plated @ 20,000 cells in DMEM and 5% fetal bovine Serum in a 48-well plate. Cells were spin-transfected and incubated overnight with fluorescein labeled non-specific siRNA (Cell Signaling) conjugated to BAFF receptor specific mAb. After 24 h, cells were protease treated, washed, cytospun, and immediately observed under fluorescence Olympus microscope. The inventors did not measure BAFF receptor mRNA inhibition in these cells as the inventors have used nonspecific, non-targeting siRNA to conjugate the BAFF receptor mAb, in this particular experiment.

Dose optimization, treatment and therapeutic evaluation of EAMG mice. Two weeks after the $2^{nd}$ booster immunization with CFA-AChR, EAMG mice with clinical signs of established disease were randomized for treatment. Each group of mice (n=4 per group, for dose optimization only) were either left untreated or treated intraperitoneally (i.p.) with BAFF receptor specific mAb-siRNA conjugate at 50 µg, 125 µg or 350 µg per 25 g body weight of each mouse. To determine the most effective dose (maximum suppression of BAFF receptor within the limit of experiment), mice were bled from the tail vein at 2 weeks post treatment, for this experiment. PBMCs were isolated for assessment of BAFF receptor specific mRNA inhibition by real-time SYBR green PCR and flow cytometry.

To evaluate the therapeutic effect, EAMG mice were randomly distributed into groups (n=6 per group). Each group of mice was either not treated or treated i.p. with either 125 µg each unmodified siRNA-, IgG control, mAb, or mAb-siRNA conjugate at 125 µg (smt2, low or moderate dose group) and 350 µg (smt1, high dose group), per mouse. Conjugates were re-suspended in endotoxin free PBS and the mice were treated once a week for 3 weeks. The clinical grade of treated/untreated EAMG mice were recorded by blinded observation. Grip strength of mice was taken using a digital Dynamometer once a week, 4 times in 9 weeks. All mice were bled from the tail vein thrice during the course of treatment to monitor serum anti-AChR autoantibody levels. Prior to euthanasia on week 9 post treatment, mice were bled on week 8 to also assess cytokine levels in plasma (eBioscience). PBMCs were isolated by using LymphoPrep and B cells by a magnetic bead B cell purification kit (StemCell Technologies). Splenocytes and lymph node cells were prepared for flow analysis as taught by the present inventors [13].

PCR, Flow cytometry, ELISA and Radioimmunoassay. Y3 GFP+B cells, PBMCs, splenocytes, and lymph node cells were analyzed for B cell surface expression of CD268 (BAFF receptor), CD19, B220, CD95 (Fas receptor, APO-1, TNFRSF6), GL7, and other molecules by staining with fluorochrome labeled antibodies. PBMCs were washed with PBS-1% FCS, stained with mAb specific for BAFF receptor (LS Bioscience), a PE-conjugated secondary antibody, and also an APC-conjugated CD19 specific antibody. Cells were either analyzed immediately or fixed in 1% paraformaldehyde for flow cytometry analysis.

RNA from PBMCs and from pieces of snap frozen spleen and lymph nodes (inguinal) were isolated using Trizol purchased from Invitrogen (Carlsbad, Calif.). DNA-free cDNAs were prepared from RNA using Superscript II, random primers, nucleotide mix, DNAse, and appropriate buffers (Thermo Fisher) [13]. Relative expression of BAFF receptor, CD19, B220, IFN ($\alpha$,$\beta$), and Beta actin (for normalization) were analyzed by using FAM-conjugated gene specific probe-primer mix and AmpliTaq Gold Taqman PCR master mix (Life Technologies) on a CFX 96 Real-Time system (Biorad, Hercules, Calif.).

ELISA assay and high affinity Ab assay were performed with serum using the antibodies and the method the inventors described in detail previously [12]. Briefly, to measure the level of high affinity anti-AChR Ab, normal mouse AChR (0.5 µg/mL) was used as a coating antigen. Serum was used at a dilution of 1:2000 in PBS. HRP-conjugated rat anti-mouse IgG1, IgG, IgM, and IgG2b (Caltag and BD Bioscience) were used at 1:1000 dilution and ABTS as a substrate for ELISA. To determine if the conjugate treatment has altered the AChR binding affinity of anti-AChR Ab in EAMG mice, mouse muscle AChR prepared from normal C57BL6/J mice was labeled with [125I]$\alpha$-bungarotoxin (BTX) (PerkinElmer, Waltham, Mass.) and incubated with serum from experimental mice to allow binding of AChR specific antibody with radiolabeled AChR in competition with normal mouse serum. The Ag-Ab complex was then precipitated with polyclonal rabbit anti-mouse Ab, washed and counted in a $\gamma$ counter for [125I]$\alpha$ BTX bound to serum.

Immunocytochemistry. For immunocytochemistry, fluorescent-conjugate treated GFP-cells, purified B cells (Stem cell Tech) or PBMCs were stained with Hoechst (or not) (Thermo Fisher). Cells were cytospun on the adhesive coated slides, and either directly or after mounting on an anti-fade mounting medium, were immediately observed under an Olympus microscope. To determine conjugate induced cell death, GFP+ cells were also stained with propidium iodide (Biolegend) for 10 minutes at 4 degree C. and observed under microscope to score the percentages of apoptotic cells.

Statistical analysis. Group comparison of clinical scores and all other data were performed using Student's t-test, multiple comparison test, Mann-Whitney U test or one-way analysis of variance, where applicable. In any figure, the vertical bars represents standard errors and calculated P values denote significance at <0.05 (*), <0.01 (), and 0.001(*).

Figure 1B:
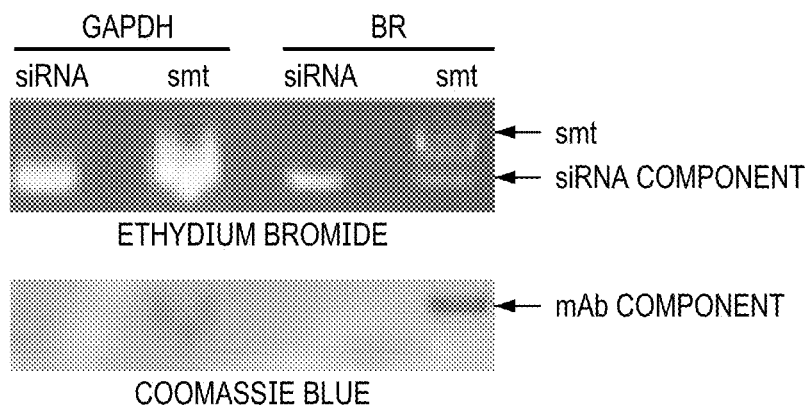
Figure 1C:
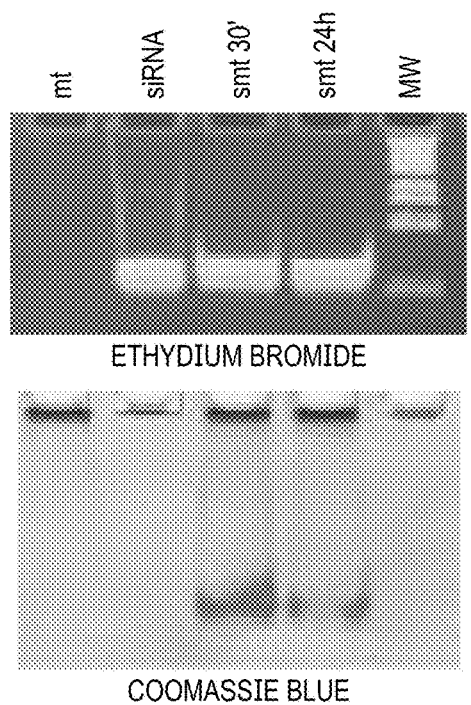

Verification of BAFF receptor specific mAb-siRNA conjugates (smt). The inventors conjugated BAFF receptor specific mAb and siRNA by using protamine and linkers, and tested BAFF receptor suppressive function of the conjugate in vitro and ex vivo. A schematic diagram of conjugate preparation is shown in FIG. 1A. A bovine IgG was also conjugated to a GAPDH specific siRNA for use as a control conjugate. Due to an increase in molecular weight, the conjugate was shifted in the gel compared to both unconjugated mAb and siRNA (FIG. 1B). Conjugate formation was further confirmed by de-staining ethidium bromide and re-staining the gel in Coomassie blue to reveal the presence of mAb protein as higher molecular weight bands (lower panel). Protamine non-coupled siRNA did not form conjugate complex with mAb (not shown). The stability of BAFF receptor specific conjugate was also determined (FIG. 1C). Purified conjugates were then used in vitro for functional studies and administered i.p. in EAMG mice for evaluation of their therapeutic effect.

Confirmation of receptor mediated endocytosis of mAb-siRNA conjugate into B cells, in vitro and ex vivo. Next, the inventors determined the ability of BAFF receptor specific conjugate to internalize into B cells for mRNA inhibition. For this, the inventors prepared a conjugate consisting of BAFF receptor specific mAb and Cy-3 labeled non-specific siRNA to transfect with a rat myeloma Y3 cell line that was stably transduced with bicistronic retrovirus for high-level coexpression of BAFF receptor transgene and GFP [6]. To confirm conjugate-internalization ex vivo, magnetically purified CD19+B220+B cells from EAMG mice were transfected with conjugate consisting of BAFF receptor specific mAb and fluorescein labeled non-specific siRNA. For detection of intracellular fluorescence from live cells and also to protect viability of cells from any nonspecific toxic effect that may arise from the fluorescent siRNA component in the conjugate, incubation times did not exceed 24 h.

Figure 2A:
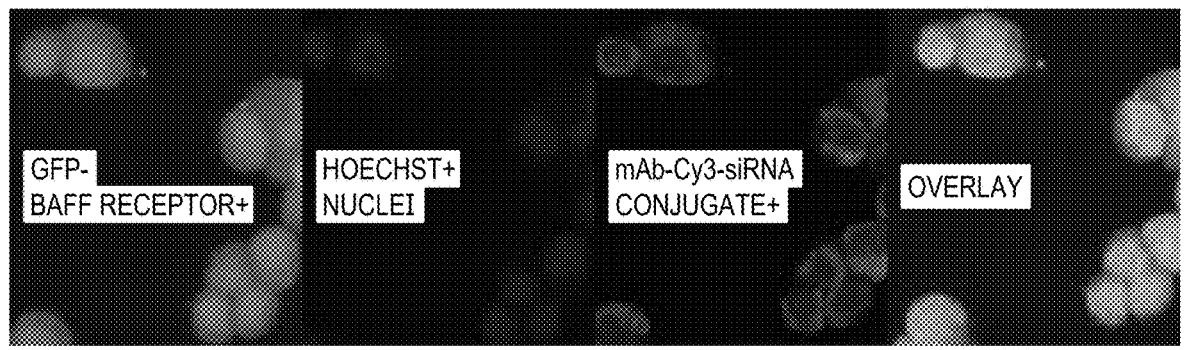
FIGS. 2A and 2B show receptor mediated endocytosis of BAFF receptor conjugate.
Figure 2B:
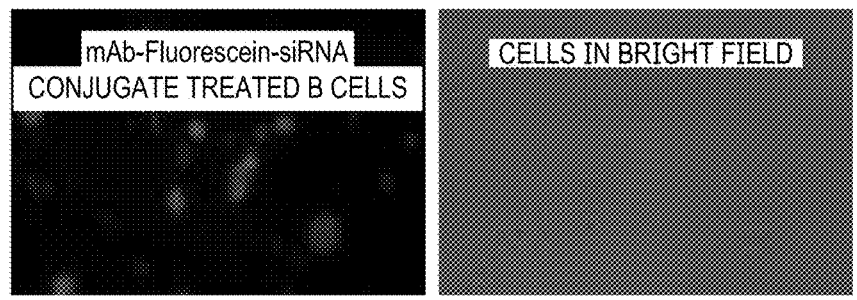

The results show that approximately 80% of Y3 cells and 70% of B cells emitted red (FIG. 2A right panel) or green fluorescence (FIG. 2B, left panel), due to uptake of the conjugates that contained Cy-3 or fluorescein siRNAs, respectively. The overlay in FIG. 2A represents cytosolic accumulation of Cy-3 containing conjugates surrounding the Hoechst blue fluorescence positive live cell nucleus.

Figure 3A:
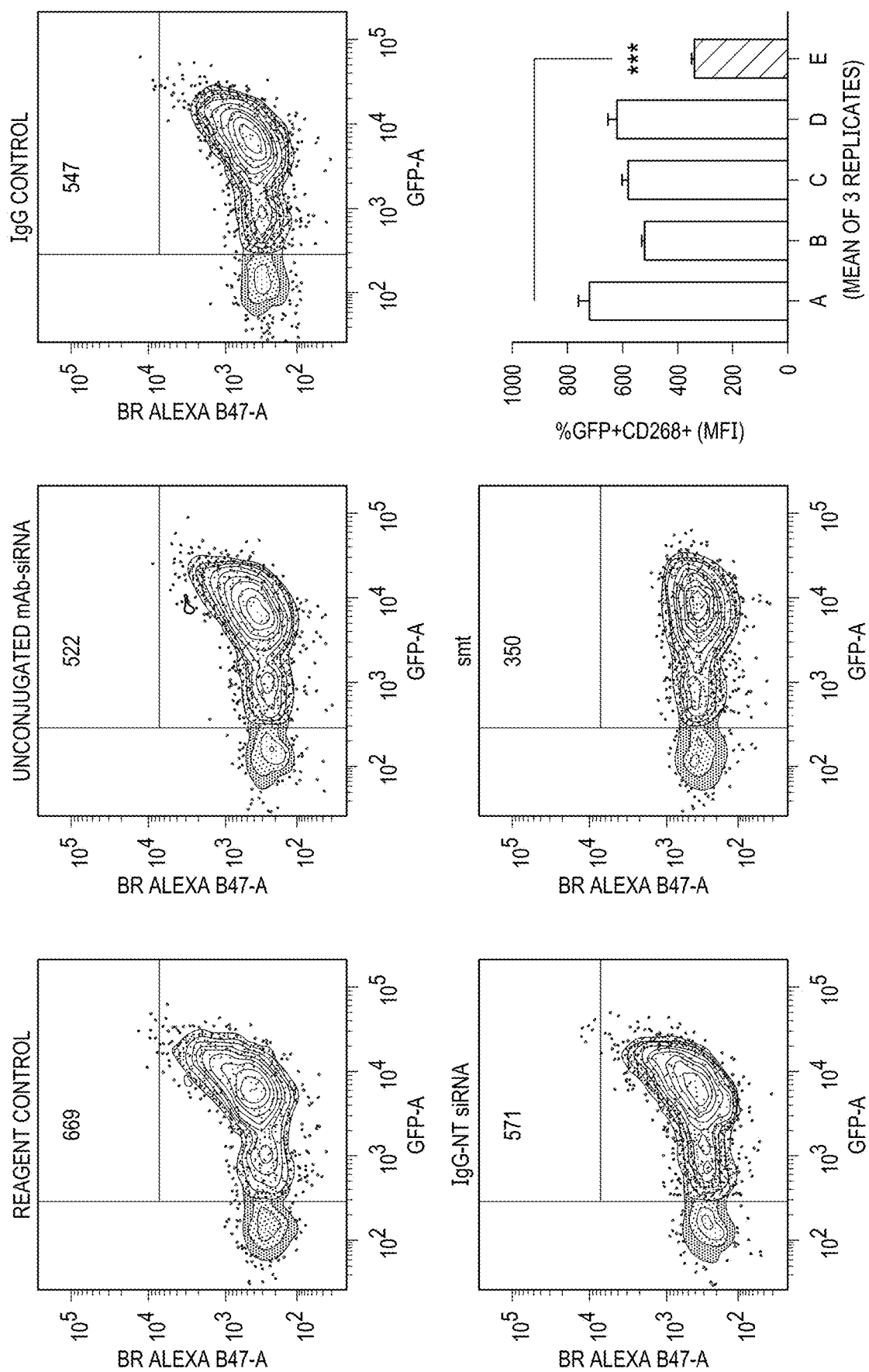
FIGS. 3A to 3C shows the results of conjugate mediated reduction of BAFF receptor in vitro and in vivo dose kinetics.

Validation of BAFF receptor reduction by the conjugate, in vitro and in vivo. To ensure that internalization of conjugate results in siRNA mediated mRNA degradation and the resultant reduction of BAFF receptor expression in mature B cells, Y3 cells were incubated either with BAFF receptor specific conjugate or siRNA-, IgG- and IgG-siRNA conjugate controls for 48 hours. Flow analysis revealed close to 50% reduction of BAFF receptor expression (in live cells) by the conjugates compared to untreated or other controls. In all three experimental replicates, the BAFF receptor conjugate significantly reduced CD268+CD19+Y3 B cells compared to respective controls (FIG. 3A).

Figure 3B:
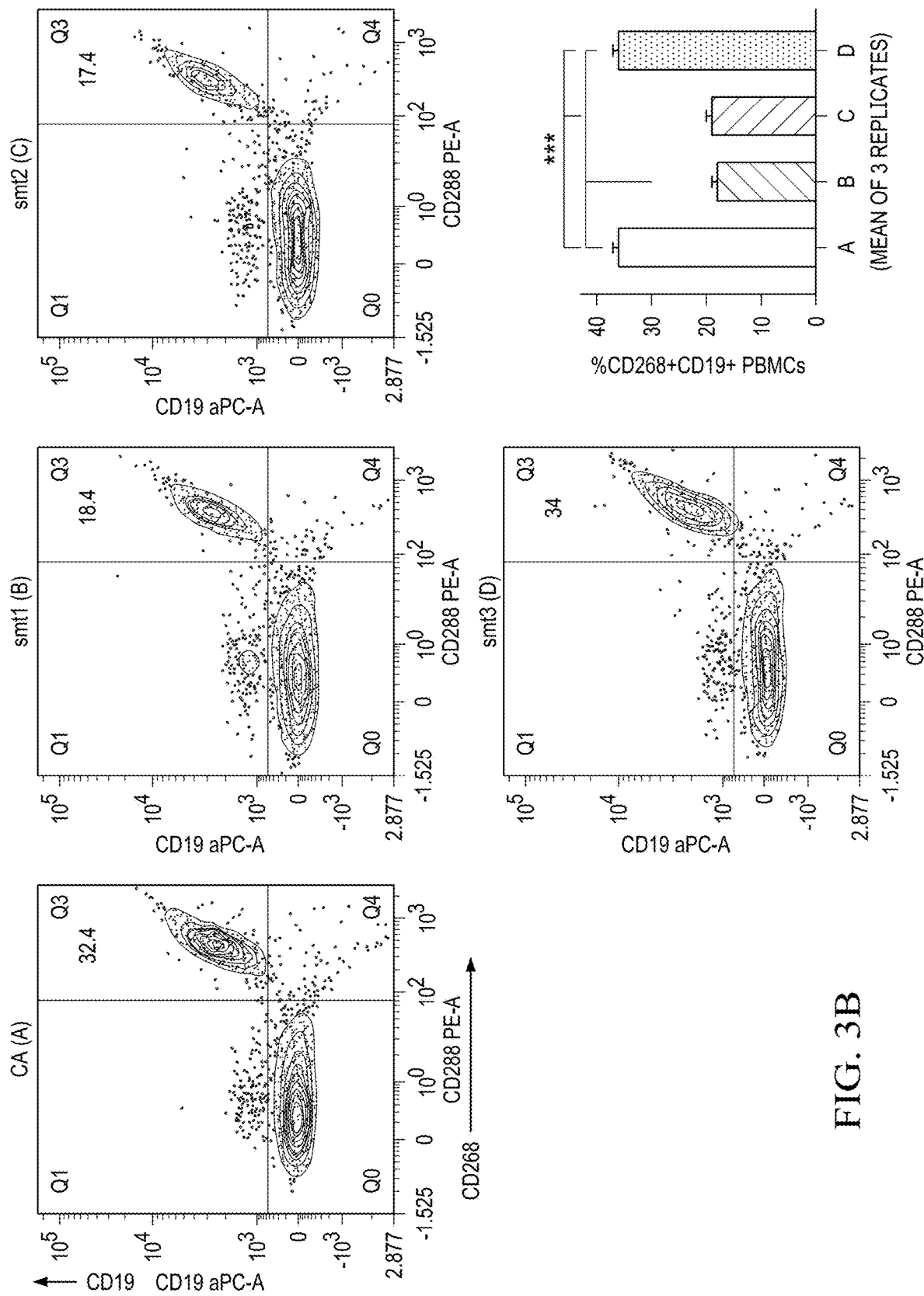

The inventors further confirmed the receptor inhibitory effect of BAFF receptor specific conjugate in vivo. The conjugate was administered intraperitoneally (i.p.) in EAMG mice with established disease (post $2^{nd}$ booster immunization) at three different doses. For dose optimization, groups of EAMG mice were treated i.p. with conjugate at three doses only once, for this particular experiment. Doses used were: smt1, high dose, 350 µg each mAb and siRNA; smt2, low dose A, 125 µg of each mAb and siRNA; smt3, low dose B, 50 µg of each component of the conjugate for each mouse of about 25 g of body weight. All mice were bled to harvest PBMCs at 2 weeks post treatment based on the inventors' prior observation of persistence of siRNA inhibitory effect until this time point [13]. As shown in FIG. 3B, the BAFF receptor conjugate at either 125 µg or 350 µg (i.e. 5 mg or 13 mg per Kg respectively) a greater number of mature B cells (CD268+CD19+) compared to those untreated or treated with bovine IgG controls. Notably, the frequency of BAFF receptor expressing cells in both dose groups was comparable in PBMCs. Both doses were well tolerated by EAMG mice. The conjugate mediated effect was not drastic in PBMCs due possibly to the presence of cell pools other than mature B cells in PBMCs.

Figure 3C:
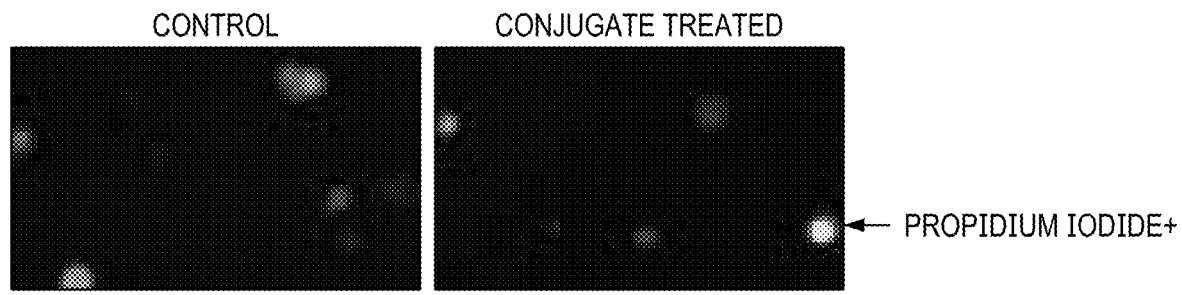

The inventors also determined if the BAFF receptor specific conjugate induced apoptotic cell death. These results show that BAFF receptor conjugate indeed, in addition to significant suppression of the receptor, induced cell death in Y3 cells. These results shows higher frequency (20%) of propidium iodide stained peripheral apoptotic B cells induced by conjugate treatment (FIG. 3C).

Figure 4A:
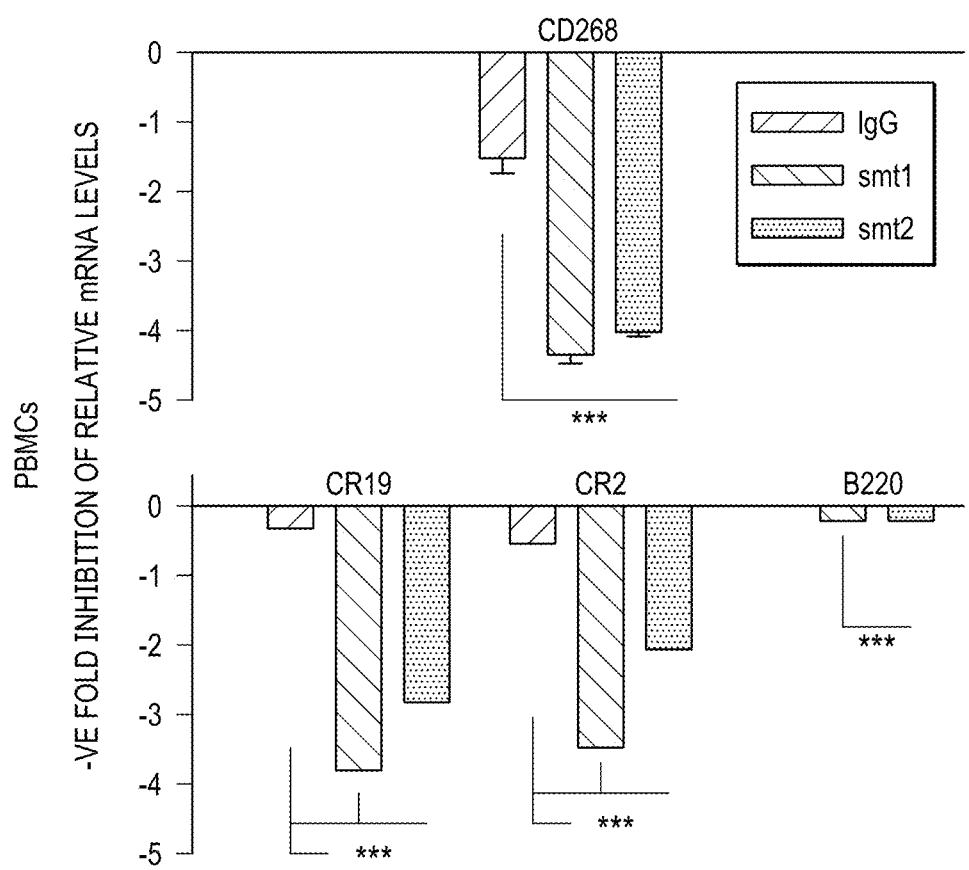

BAFF receptor conjugates reduced BAFF receptor and B cell antigens expression and at high dose, (smt1) triggers excessive Fas expression in CD19+ and B220+ cells in lymph node. Since at a dose of 350 µg and 125 µg, conjugate was found to exert comparable effects (percent reduction of CD19+CD268+ cells in PBMCs), the inventors next evaluated the therapeutic effect of conjugates at both the doses. In a separate experiment with a larger sample size per group (n=6), the inventors treated EAMG mice with conjugate once weekly for 3 weeks and bled animals at 8 weeks post treatment to assess the relative reduction of BAFF receptor and other B cell receptors. Conjugate treatment significantly reduced relative expression of BAFF receptor (normalized level nearly 4.5 fold) as well as the levels of CD19, B220 and CR2 (complement receptor) in PBMCs as compared to untreated controls, at that time point (FIG. 4A). B cell surface antigens, CD19, B220, and CR2 were also suppressed, possibly due to a cell depletion effect of the BAFF receptor specific conjugate.

Figures 1, 4B:
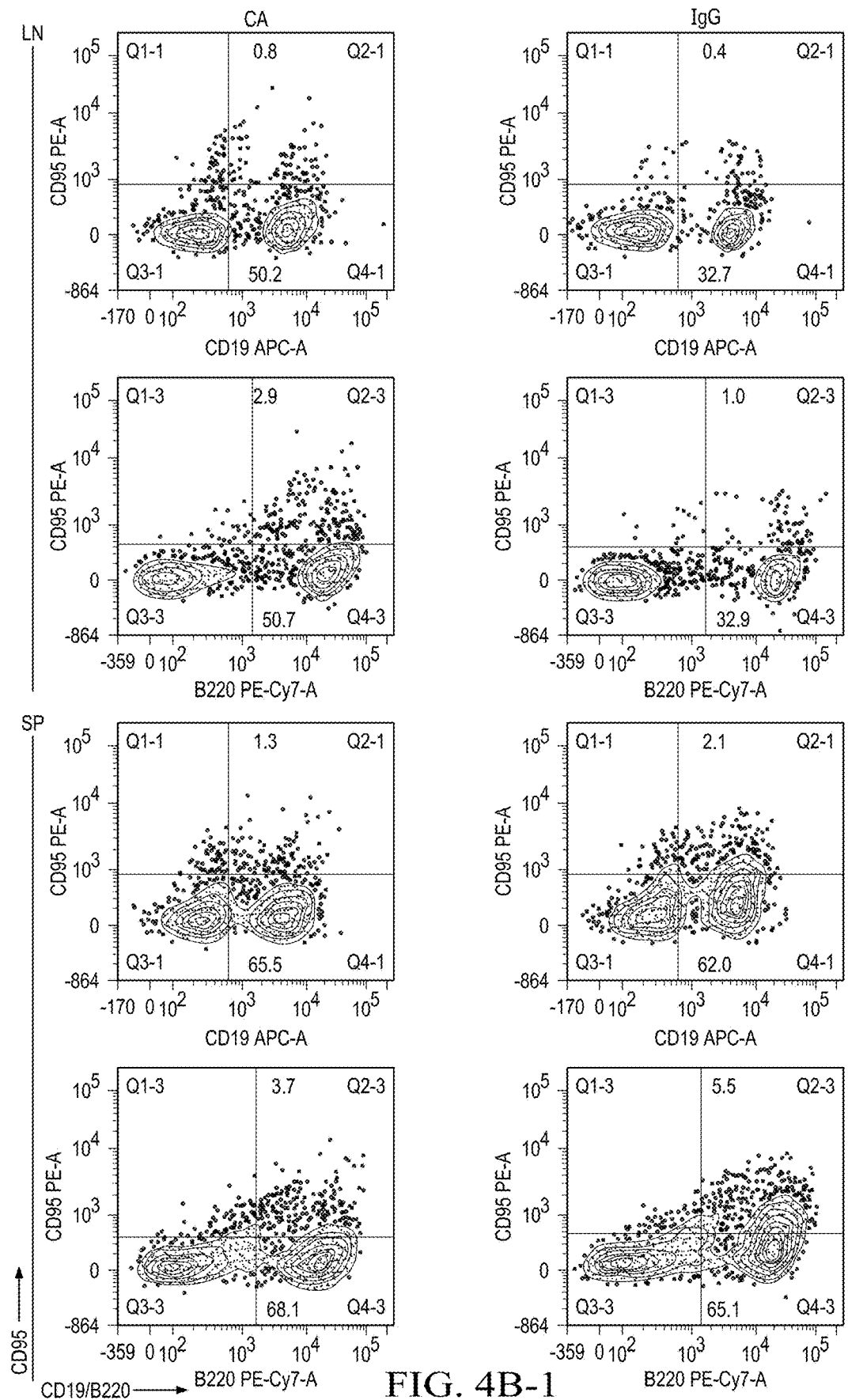
Figures 2, 4B:
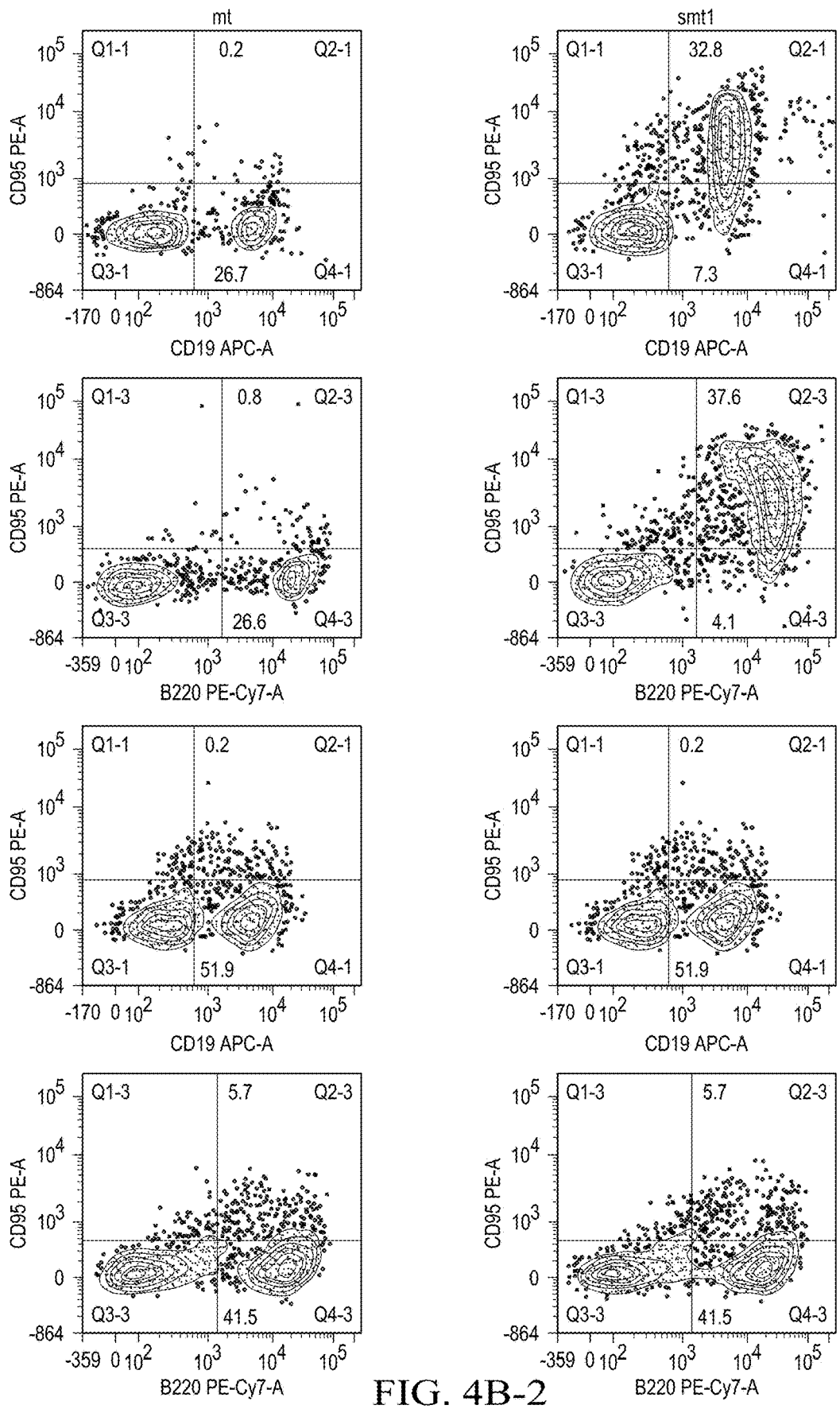
Figures 3, 4B:
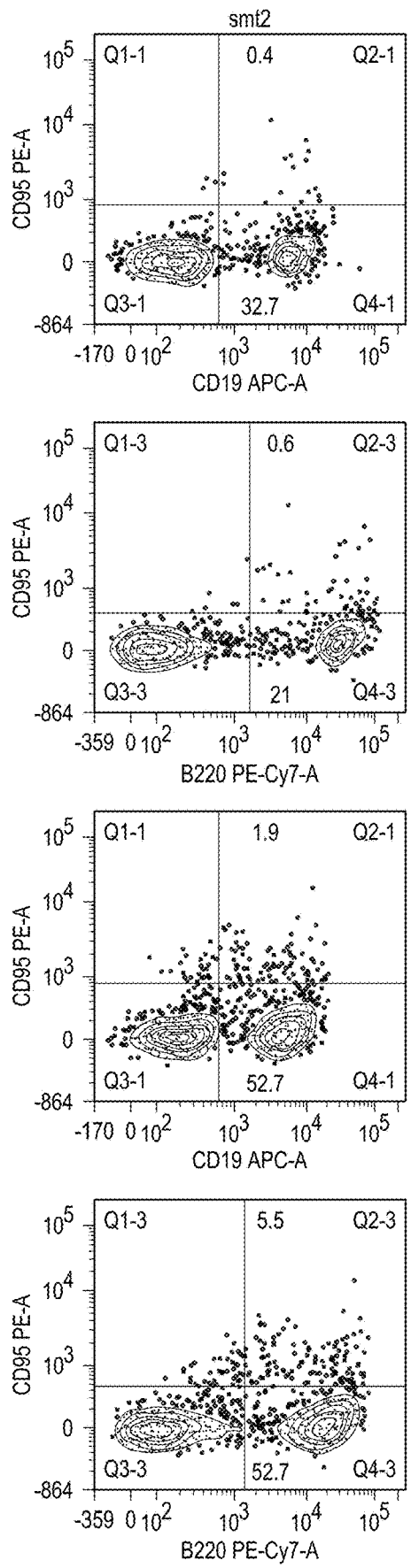

Next, the inventors tracked the relative distribution of conjugate in secondary lymphoid organs. To analyze the inhibitory effect of BAFF receptor conjugate on splenic and lymph node B cells, EAMG mice were euthanized during the $9^{th}$ week post treatment. Flow cytometry was performed to analyze surface co-expression levels of BAFF receptor and B cell specific markers, and revealed marked reduction of CD268+CD19+ and CD268+B220+ cells in lymph nodes and spleen of conjugate treated mice, relative to other controls (FIG. 4B). Notably, low dose (smt2) resulted in marked deficiency of CD268+ cells in lymph node as compared to high dose (smt1). The result was also intriguing as the effect of conjugate on BAFF receptor suppression was found to be long lasting, even after 8 weeks of treatment that again appears to have been mediated by the B cell depletion effect of the conjugate.

Figure 4C:
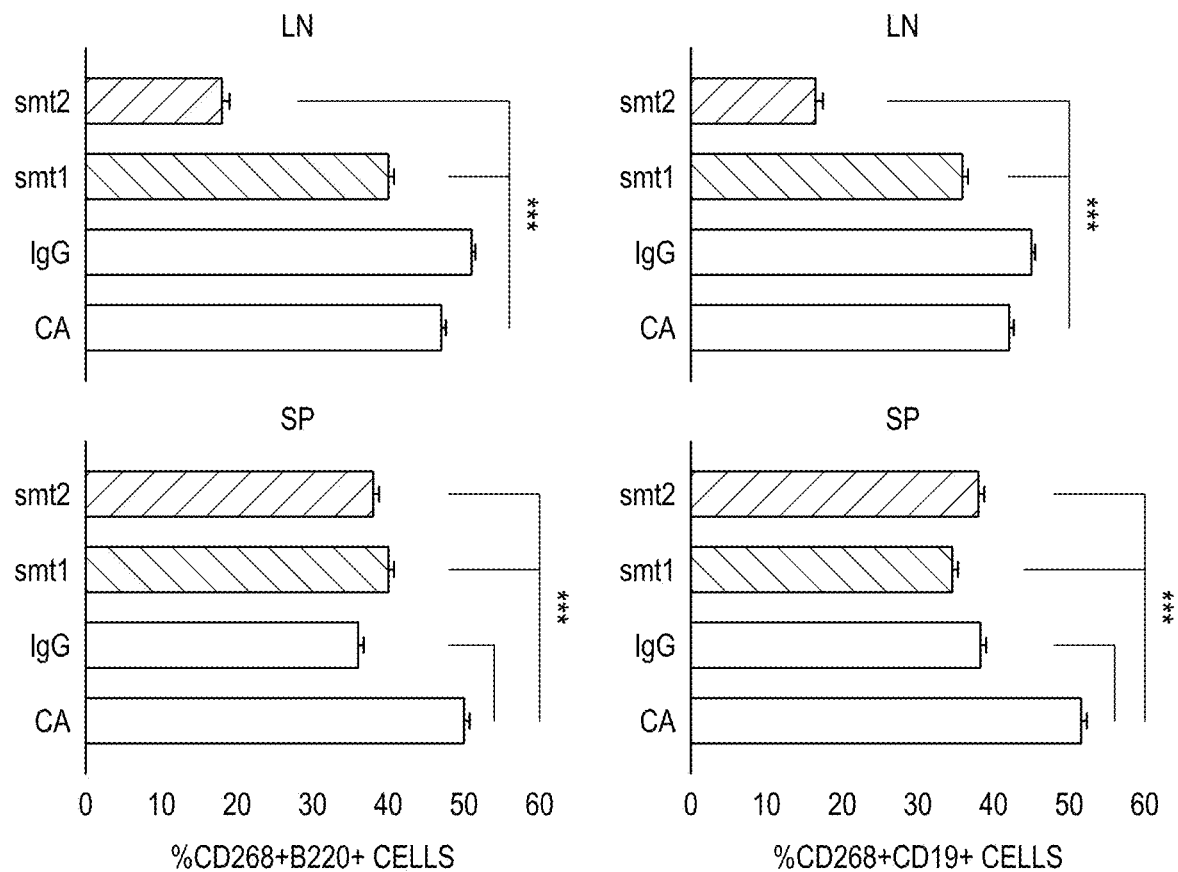

To further evaluate B cell phenotypes and gross survival effect of BAFF receptor conjugate in splenic and lymph node B cells, the inventors examined expression levels of Fas (CD95) in those cells, as this protein is known to express in germinal center B cells only after induction of cell death [14, 15]. Strikingly, the inventors found significant accumulation of Fas expressing CD19+ and B220+ cell population in lymph nodes but not in spleen of solely high dose conjugate (smt1)-treated EAMG mice (FIG. 4C). Low dose (smt2) conjugate did not induce Fas expression in lymph nodes.

Figure 4D:
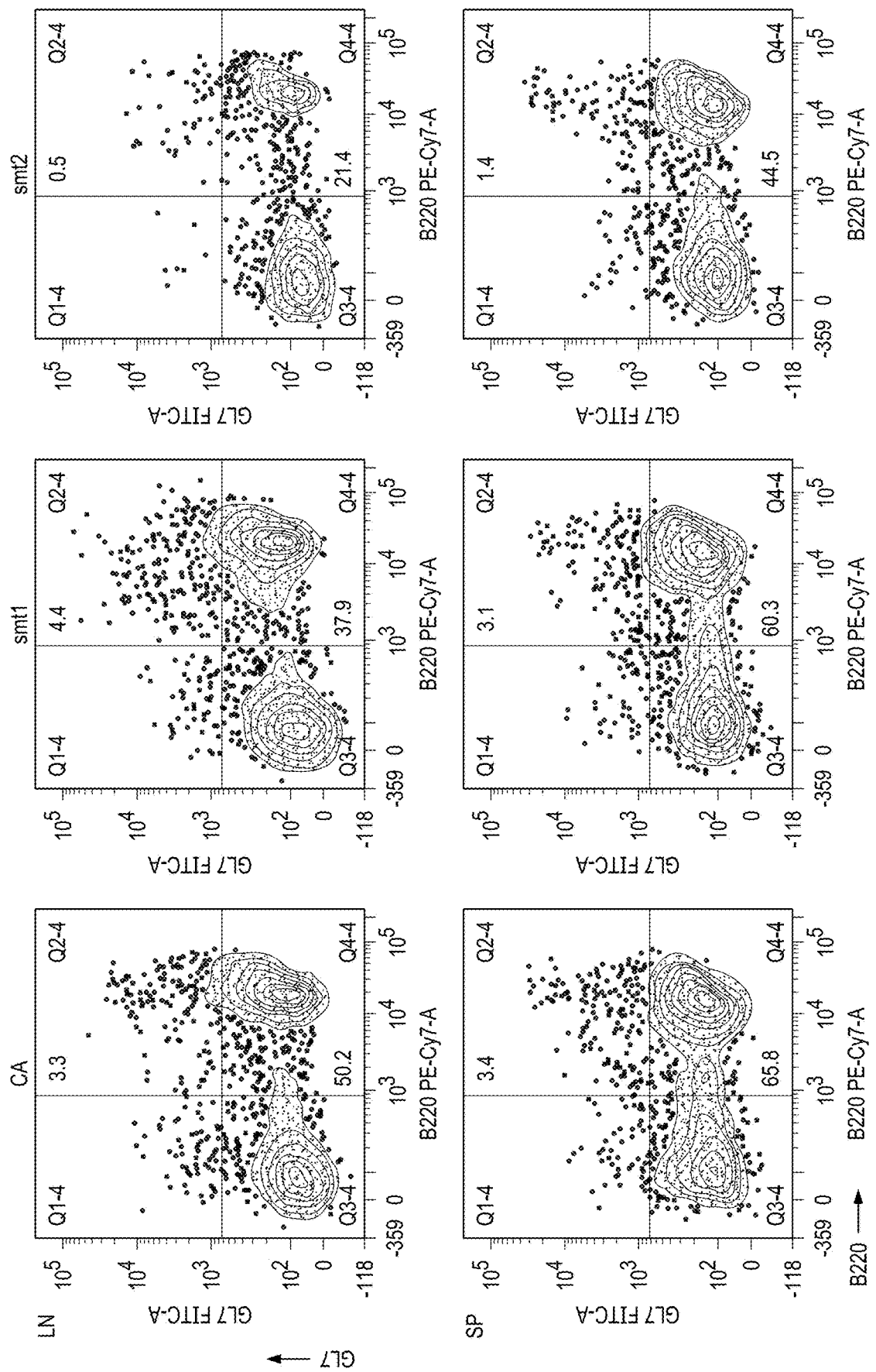

GL7 is known to be expressed by activated T cells and B cells [16]. To determine the fraction of activated splenic and lymph node cells, the inventors also checked coexpression of GL7 and B220 in the lymph node following conjugate treatment. The inventors found that GL7 expression is minimally expressed in smt2 and the differential expression is not significant over untreated EAMG controls (FIG. 4D). FIG. 4E is a graph that shows the percent positive cells for CD3, CD11c or CD19.

Figure 5A:
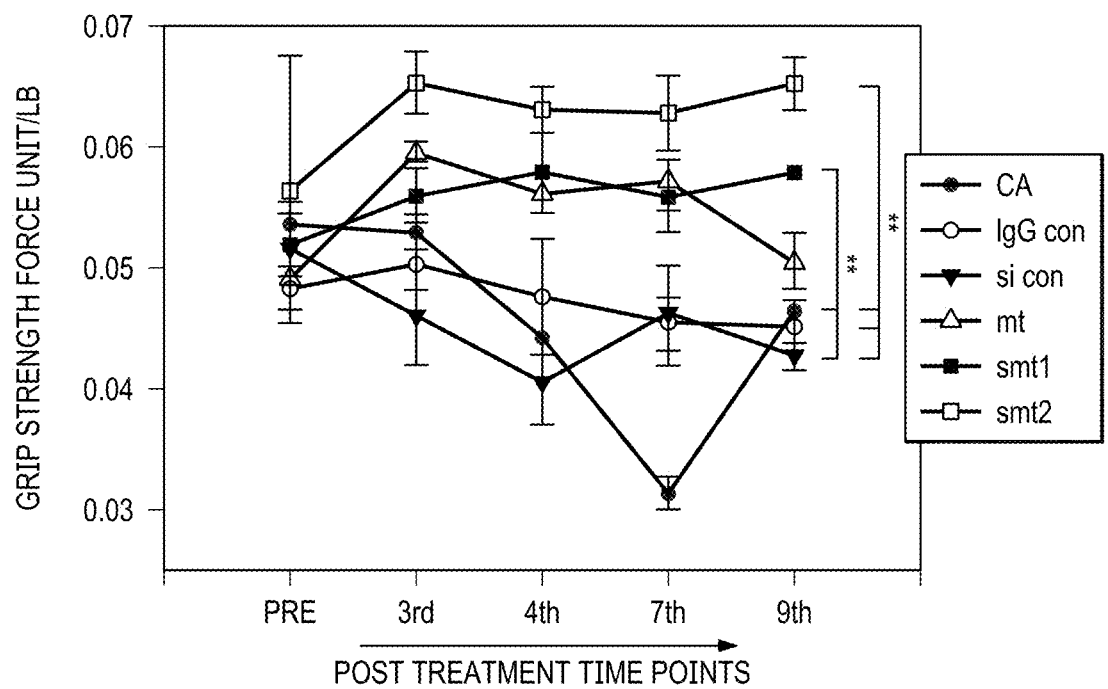
FIGS. 5A and 5B shows the evaluation of therapeutic effect of BAFF receptor specific conjugates in EAMG.
Figure 5B:
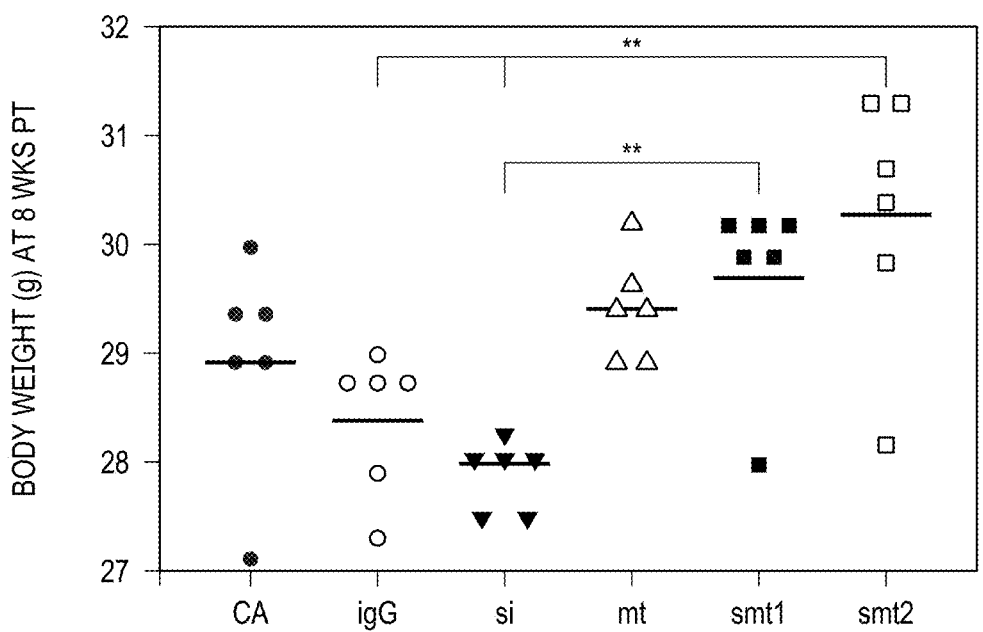

BAFF receptor conjugate significantly improve muscle-grip strength of EAMG mice. EAMG mice with established disease (post $2^{nd}$ booster immunization) was treated with BAFF receptor conjugate at two doses, 125 µg and 350 µg per 25 g (i.e. 5 mg and 14 mg/Kg, respectively) of body weight, which previously showed comparable levels of BAFF receptor reduction in CD19+B cells of PBMCs and in spleen. All mice were treated once weekly for 3 weeks. Groups of mice were also treated with unconjugated bovine IgG-, mAb or siRNA controls, once weekly for 3 weeks. Digital recording (Dynamometer) of grip strength once during weeks 3, 4, 7, and 9 revealed significant improvements in muscle strength of mice treated with BAFF receptor conjugates as compared to other treatment or control groups. The result demonstrates that BAFF receptor conjugate is effective in improving muscle strength in EAMG mice. Notably, the grip strength of mice receiving conjugates at low dose (smt2) did not differ significantly than those that received twice or more the dose (smt1) (FIG. 5A). Neither the disease symptoms nor the grip strength values in other groups were different at any post treatment time points. The mean body weights of the conjugate treated mice were slightly higher compared to other groups (p=0.04) (FIG. 5B).

Figure 6A:
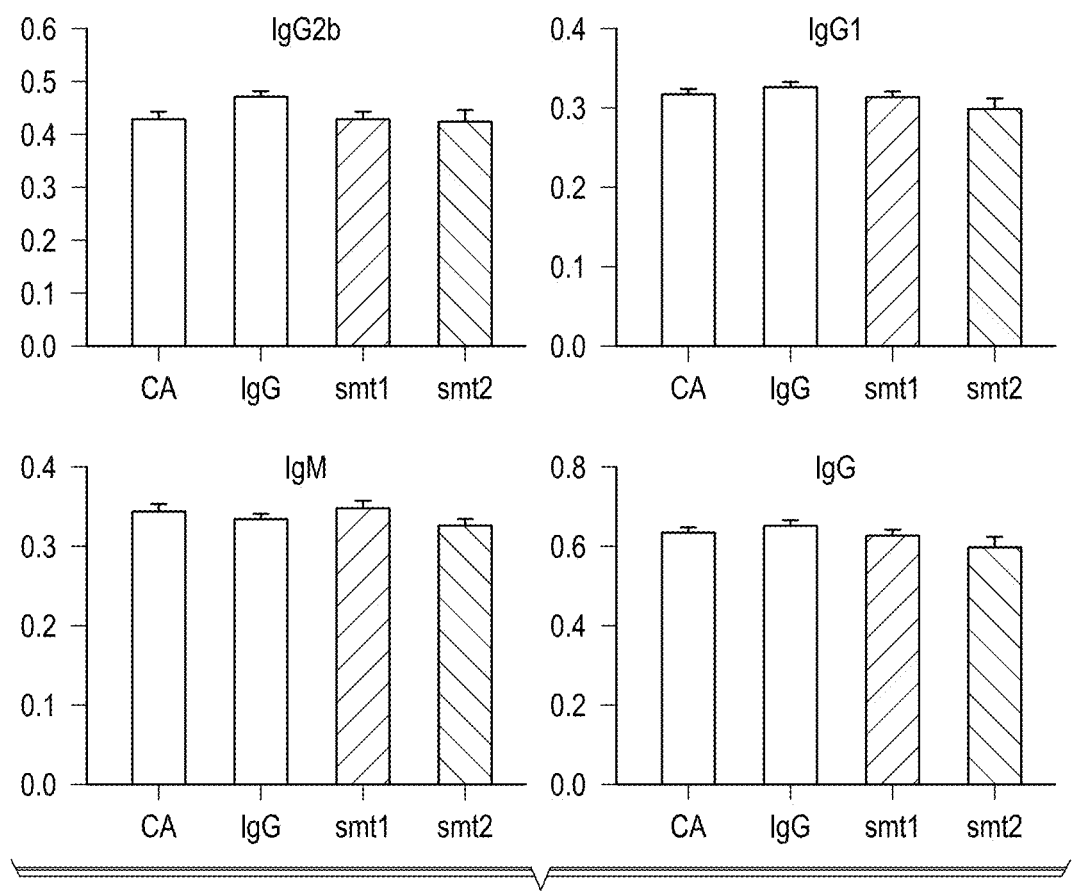
FIGS. 6A and 6B show serum anti-AChR antibody levels and antigen specific affinity of auto-antibody in untreated and conjugate treated mice.
Figure 6B:
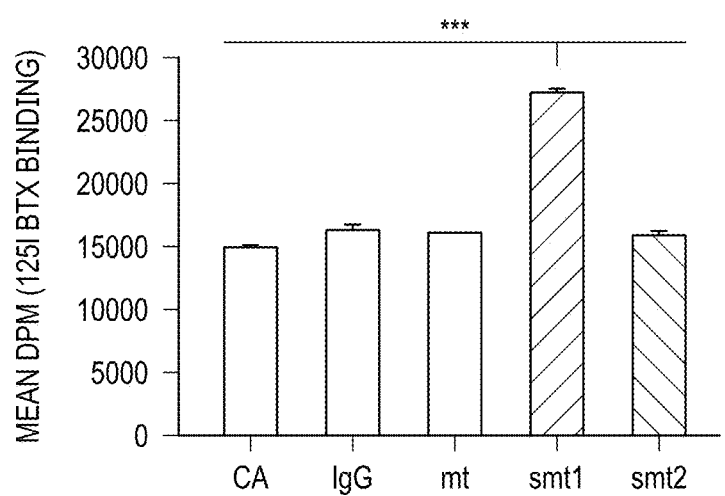

BAFF receptor conjugate did not reduce serum level of anti-AChR autoantibody in EAMG mice. Immunizing mice with torpedo-AChR induces generation of pathogenic, complement fixing, anti-AChR autoantibody that binds to nicotinic AChR at the post synaptic neuromuscular junctions of muscle. Through crosslinking of AChR or formation of membrane attack complex, the autoantibody then depletes myocytes of AChR or prevents binding of acetylcholine to AChR that ultimately results in muscle weakness. To elucidate if BAFF receptor specific conjugate improves EAMG by reducing the level of autoantibody, EAMG mice untreated or treated with BAFF receptor specific conjugate once weekly for 3 weeks were bled from the tail vein thrice post treatment (at weeks 3, 5, 8). Serum anti-AChR Ig subtypes and pathogenic anti-AChR IgG2b levels were measured by ELISA analyses. Unexpectedly, at any post treatment time-point tested, conjugate treatment consistently failed to reduce anti-AChR Ab isotypes including pathogenic isotype, IgG2b levels (FIG. 6A). Moreover, by using 125I α-Bungarotoxin labeled normal mouse AChR in a radioimmunoassay, high affinity AChR specific Ab was detected in serum of high dose conjugate treated mice (FIG. 6B).

Figure 7A:
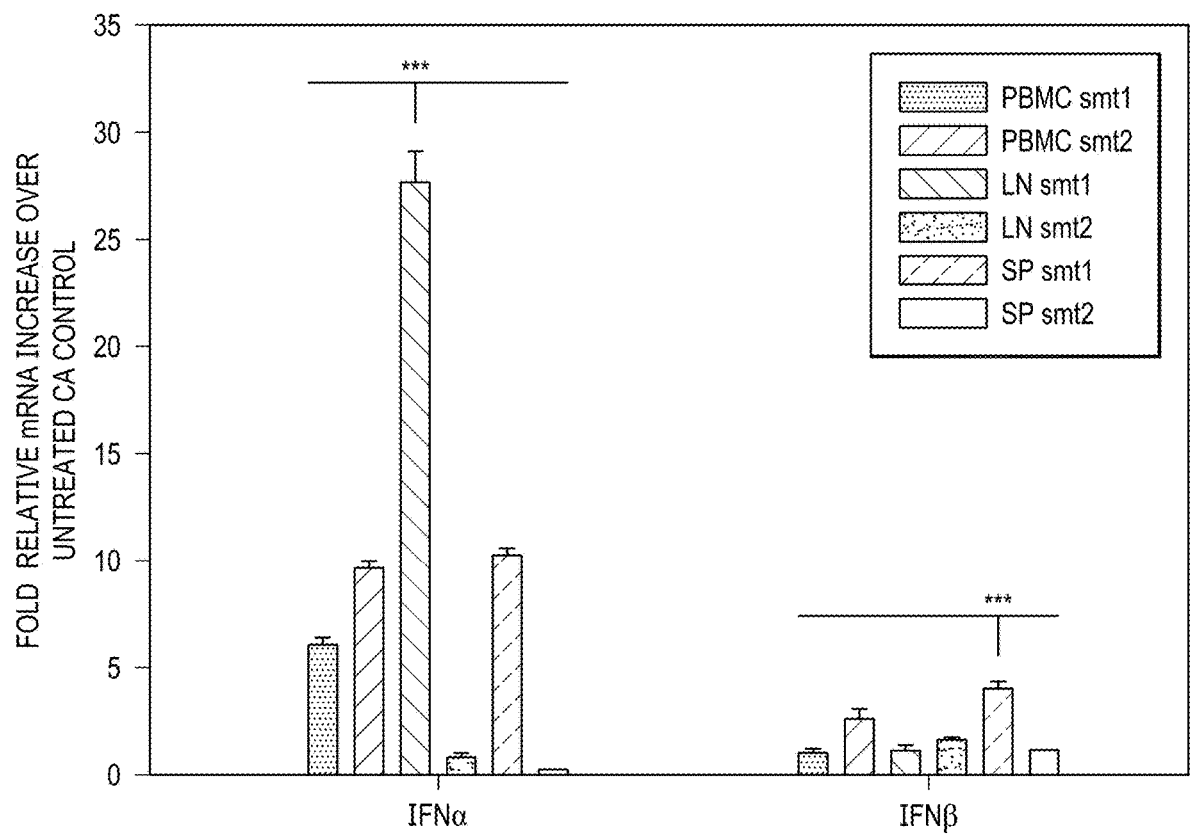
FIGS. 7A and 7B show cytokine expression and serum cytokine level in EAMG mice treated with conjugates.
Figure 7B:
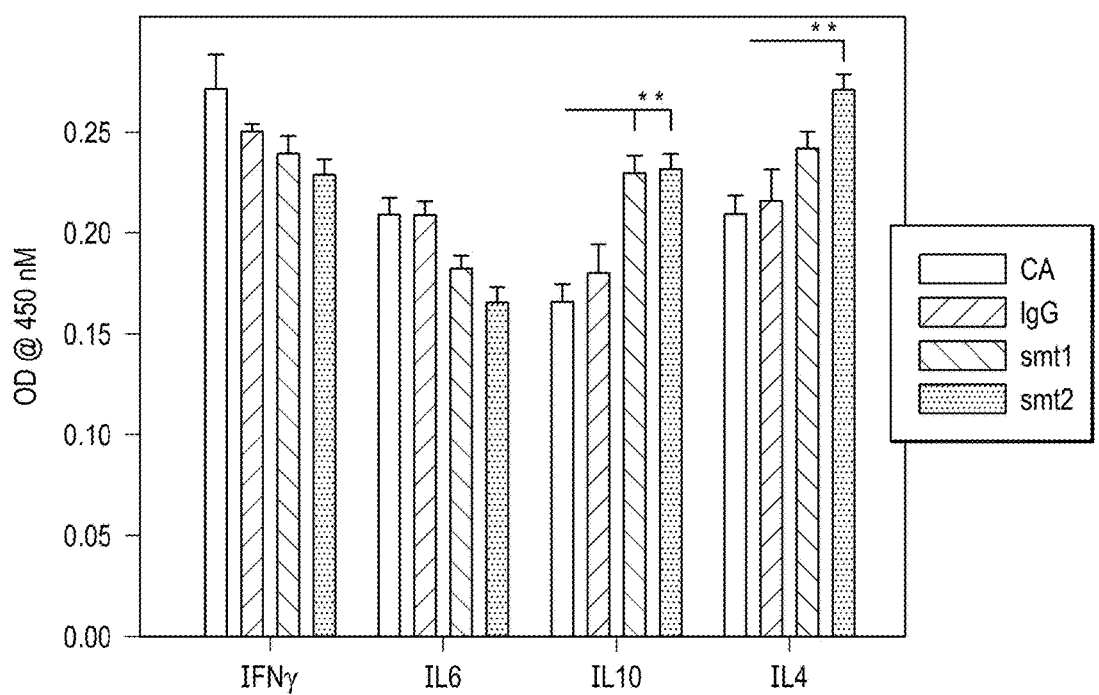

Type I interferon expression and serum cytokine levels. The inventors have previously demonstrated that through regulation of inflammatory milieu, certain cytokines play a profound role in EAMG pathogenesis [17]. To further explore what may have contributed to the observed balance in serum anti AChR antibody levels or upregulated anti-AChR antibody affinity by high dose BAFF receptor conjugate treatment, the inventors first measured type 1 interferon (IFN) expression in PBMCs and lymphoid cells in mice. Type 1IFN has been shown to modulate autoantibody production through AChR production from thymic epithelial cells [18]. IFN also plays a role in inducing apoptosis through ISG stimulated genes [19]. An abnormally high expression of IFNα was detected in the lymph node of high dose conjugate treated EAMG mice (FIG. 7). Unlike type 1 IFN, both mRNA and secretory protein levels of IFNγ remained low and similar between untreated and conjugate (smt1 and smt2) treated EAMG mice. IFNα and IFN mRNA levels also moderately increased in spleen of high dose conjugate treated mice. In contrast, expression of IFN β, but not IFNα was found to increase predominantly in PBMCs of low dose conjugate treated mice.

To further identify an effect of the conjugate on serum cytokines and to correlate the serum anti-AChR antibody levels with cytokine production in treated EAMG mice, the inventors measured both the serum levels and relative mRNA levels of IL6, IL10, IL4 in PBMCs and secondary lymphoid organs. ELISA analyses revealed significant increase in IL10 and IL4 levels in conjugate treated mice over untreated and other control samples (FIG. 7). However there was a discrepancy between mRNA levels in PBMCs and serum levels of IL6. Increased mRNA levels of IL6 (not shown) in PBMCs of conjugate treated mice may have resulted from mRNA stabilization that consequently resulted in the production of slightly lower level of IL6 in serum of conjugate treated mice.

In this study the inventors assessed in EAMG mice the therapeutic effect of inhibiting the BAFF receptor with a BAFF receptor specific mAb-siRNA conjugate. The inventors chose to use whole mAb (rather than its fragment) to mimic current clinical treatments for MG and study the consequences of cell specific treatment. The inventors also reasoned that conjugate therapy will not form post-treatment immune-complexes due to unavailability of unconjugated free antibody and its interaction with the soluble receptors. Additionally, the inventors reasoned that due to the preservation of a peritoneum-residing, protective B (B1) cell population that lacks BAFF receptor, innate immunity would not be affected [6,20]. As expected, the inventors found significant depletion of BAFF receptor in PBMCs, lymph node cells and splenocytes in EAMG mice and also in vitro with Y3 cells following this conjugate treatment. However, in vivo BAFF receptor reduction by the conjugate did not result in complete remission of disease in EAMG mice, likely due to a pleiotropic effect of the conjugate in vivo. Surprising and unexpected findings included a marked increase in the number of Fas expressing cells, IFN overexpression in lymph node, and high affinity serum anti-AChR Ab in association with high dose conjugate treatment. By contrast, low dose conjugate treatment elicited a higher level reduction of BAFF receptor in lymph nodes, improved grip strength and greater body weight of EAMG mice post therapy, without a reduction in serum level of pathogenic antibody (IgG2b), but accompanied by increased serum levels of Th2-cytokines (IL4, IL10), and decreased level of IFNγ. The skilled artisan will recognize that the dosage amount can be varied to optimize the adjuvant effect of the present invention without undue experimentation.

By way of explanation, but in no way a limitation of the present invention, distinct populations of Fas expressing cells with B cell phenotypes were found in abundance in lymph node (but not in spleen) after high dose conjugate treatment in EAMG mice, which suggests that the preferential target of the conjugate is the lymph nodes. Whether these cells are lymph node resident cells or circulatory B cells that infiltrated to the lymph node as an effect of the high dose treatment is not known, but it is plausible that the efficient uptake of conjugate by B cell at high dose induced apoptotic signaling, and this response is distinct from that elicited by low dose treatment. Low dose conjugate did not induce Fas expressing cells, revealing that high dose conjugate (smt1) drives a subset of B cells that possess enhanced sensitization to apoptotic death by dramatic upregulation of Fas and populate as B220 and CD19 co-expressing live cells in lymph nodes but not in spleen. Of note, as per manufacturer, the anti-Fas antibody used to perform flow cytometry experiment does not trigger apoptosis in any cell per se. While low dose treatment induced greater suppression of receptor that did not reach the threshold to induce apoptosis or induced mild apoptosis through a different signaling pathway, high dose treatment did induce Fas ligation that resulted in the processing of high affinity autoantibody production through elimination of less potent, autoreactive mature B cells [14].

Fas expressing lymph node cells may also be plasmacytoid dendritic like cells (pDCs) which are circulating, immature DCs that are activated by nucleotide fragments from apoptotic or necrotic cells and migrate to lymph nodes to express various surface antigens, including B220 and type 1 IFNs [21]. Increased type 1 IFN expression in the lymph nodes compared to spleen or PBMCs in high dose conjugate treated mice indicates that the potential inducer of type1 IFN could be this unique population of cells. The inventors hypothesize that the increased frequency of B cell death and apoptotic release of DNA by high dose conjugate treatment either stimulated these cell types or induced apoptotic B cells in the periphery that mimicked pDC functionality to localize inside lymph nodes. Higher frequency of these Fas expressing, specialized B cells lead to the production of high affinity autoantibody, whereas low or modest dose conjugate induced greater suppression of BAFF receptor and improved EAMG. Thus, the inventors demonstrate that siRNA directed mRNA silencing is a powerful approach as long as this effect does not trigger apoptosis or systemic release of apoptotic gene fragments, particularly in the context of therapy for autoimmune disease.

Despite reducing the receptor mRNA levels, BAFF receptor specific conjugate did not lower the level of pathogenic Ab probably due to the unexpected induction of type I IFNs that may have hindered the real-time reduction of anti-AChR Ab levels. Surprisingly, despite having high affinity Ab, the grip strength of high dose conjugate treated mice did not deteriorate significantly, an observation that puts in further doubt the relevance of anti-AChR antibody alone in influencing EAMG pathogenesis. A number of previous studies on mAb-siRNA conjugates did not report a type I IFN response, as the primary focus of those studies was to determine the extent of specific gene inhibition in target cells and assess the ultimate benefit of mAb-siRNA conjugate treatment [3-5]. Other investigators have reported target cell only production of type I IFN but overlooked distant production of IFN by the target cells. The inventors suggest that type 1 IFN, secreted from newly evolved, Fas expressing cells may have triggered enhanced activation of AChR specific B cells, compensating for the loss in the level of anti-AChR autoantibody at post treatment. Even so, type 1 IFN were shown in some studies to mediate an immunomodulating effect in autoimmune diseases that are Th1 (but not Th17) driven [19].

Interestingly, an increase in the production of anti-inflammatory Th2 cytokines (IL4, IL10) and unaltered levels of IFNγ were detected in serum of conjugate treated EAMG mice. IL4 knockout mice have been reported to develop an early and prolonged course of EAMG after AChR immunization [22, 23]. In the mouse model of MG, IL4 is therefore thought to have a protective role. Increased levels of IL4 alone, however, do not account for the improved grip strength of smt treated mice observed in this study. IL10 is generally considered an anti-inflammatory cytokine, even though several studies reported a strong correlation of higher serum IL10 level with disease severity [24, 25]. However, those studies did not demonstrate clearly whether such increased IL10 level acted to neutralize pre-existing inflammatory response or to exacerbate autoimmune disease. Other paradoxical roles of IL10 include the down regulation of Th1 cytokines and expression of MHC class II with costimulatory molecules on macrophages, and, in contrary, stimulating FCγR receptor expression on macrophages and inducing expansion of autoreactive B cells in autoimmunity [26]. Therefore, the implications of the higher serum levels of IL10 and PBMC expression of IL10 mRNA during improvement in EAMG mice after treatment with conjugate is less clear. IL6 is known to play an important role in MG pathogenesis [27]. In contrary to the serum level of reduced IL6 level, PBMC expression of IL6 mRNA was found be higher in conjugate treated mice, which implicates stabilizing of mRNA that may have resulted in a low level of IL6 in serum. However, the decrease was not statistically significant.

The inventors demonstrated for the first time a surprising and unexpected dose-mediated, Fas-dependent and -independent apoptotic signaling by a BAFF receptor specific mAb-siRNA conjugate in the treatment of MG. This study identifies a previously unknown dose dependent differential effect, as well as an offsite, immunomodulatory effect of conjugate treatment that is critically important to consider when designing a siRNA or siRNA-Antibody based therapy. These results indicate that an array of factors and complex interactions of various cell types occur in vivo that can potentially conflict with results of a test therapeutic generated in an in vitro cell model. This study shows the importance of identifying non-specific emergence of immune cells resulting from a potent therapy and elucidating the molecular mechanism underlying dose-dependent pathogenic activation of these components. Monitoring long-term persistence of such effects is also important in determining the ultimate clinical benefit of a therapeutic for an autoimmune disease.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

[1] Lindstrom J M, Seybold M E, Lennon V A, Whittingham S, Duane D D. Antibody to acetylcholine receptor in myasthenia gravis: prevalence, clinical correlates, and diagnostic value. Neurology. 1976; 26:1054-9.
[2] Huda R, Tüzün E, Christadoss P. Targeting complement system to treat myasthenia gravis. Rev Neurosci. 2014; 25(4):575-83.
[3] Song E, Zhu P, Lee S K, Chowdhury D, Kussman S, Dykxhoorn D M, Feng Y, Palliser D, Weiner D B, Shankar P, Marasco W A, Lieberman J. Antibody mediated in vivo delivery of small interfering RNAs via cell-surface receptors. Nat Biotechnol. 2005 June; 23(6):709-17
[4] Mehta G, Scheinman R I, Holers V M, Banda N K. A New Approach for the Treatment of Arthritis in Mice with a Novel Conjugate of an Anti-C5aR1 Antibody and C5 Small Interfering RNA. J Immunol. 2015 Jun. 1; 194(11): 5446-54
[5] Peer D, Zhu P, Carman C V, Lieberman J, Shimaoka M. Selective gene silencing in activated leukocytes by targeting siRNAs to the integrin lymphocyte function-associated antigen-1. Proc Natl Acad Sci USA. 2007 Mar. 6; 104(10):4095-100
[6] Rauch M, Tussiwand R, Bosco N, Rolink A G. Crucial role for BAFF-BAFF-R signaling in the survival and maintenance of mature B cells. PLoS One. 2009; 4(5): e5456.
[7] Ng L G, Sutherland A P, Newton R, Qian F, Cachero T G, Scott M L, Thompson J S, Wheway J, Chtanova T, Groom J, Sutton I J, Xin C, Tangye S G, Kalled S L, Mackay F, Mackay C R. B cell-activating factor belonging to the TNF family (BAFF)-R is the principal BAFF receptor facilitating BAFF costimulation of circulating T and B cells. J Immunol. 2004 Jul. 15; 173(2):807-17
[8] Fu L, Lin-Lee Y C, Pham L V, Tamayo A T, Yoshimura L C, Ford R J. BAFF-R promotes cell proliferation and survival through interaction with IKK beta and NF-kappa B/c-Rel in the nucleus of normal and neoplastic B-lymphoid cells. Blood. 2009 May 7; 113(19):4627-36
[9] Yan M, Brady J R, Chan B, Lee W P, Hsu B, Harless S, Cancro M, Grewal I S, Dixit V M. Identification of a novel receptor for B lymphocyte stimulator that is mutated in a mouse strain with severe B cell deficiency. Curr Biol. 2001 Oct. 2; 11(19):1547-52
[11] Toloue M M, Ford L P. Antibody targeted siRNA delivery. Methods Mol Biol. 2011; 764:123-39.
[12] Wu B, Goluszko E, Huda R, Tüzün E, Christadoss P. Experimental autoimmune myasthenia gravis in the mouse. Curr Protoc Immunol. 2013; Chapter 15, Unit 15.8:1-26
[13] Huda R, Tüzün E, Christadoss P. Complement C2 siRNA mediated therapy of myasthenia gravis in mice. J Autoimmun. 2013 May; 42:94-104
[14] Koncz G, Hueber A O. The Fas/CD95 Receptor Regulates the Death of Autoreactive B Cells and the Selection of Antigen-Specific B Cells. Front Immunol. 2012 Jul. 25; 3:207.
[15] Zhao Y, Difrancesca D, Wang X, Zarnegar R, Michalopoulos G K, Yin X M. Promotion of Fas-mediated apoptosis in Type II cells by high doses of hepatocyte growth factor bypasses the mitochondrial requirement. J Cell Physiol. 2007 November; 213 (2):556-63
[16] Naito Y, Takematsu H, Koyama S, Miyake S, Yamamoto H, Fujinawa R, Sugai M, Okuno Y, Tsujimoto G, Yamaji T, Hashimoto Y, Itohara S, Kawasaki T, Suzuki A, Kozutsumi Y. Germinal center marker GL7 probes activation-dependent repression of N-glycolylneuraminic acid, a sialic acid species involved in the negative modulation of B-cell activation. Mol Cell Biol. 2007 April; 27(8):3008-22.
[17] Tüzün E, Huda R, Christadoss P. Complement and cytokine based therapeutic strategies in myasthenia gravis. J Autoimmun. 2011; 37(2):136-43
[18] Cufi P, Dragin N, Ruhlmann N, Weiss J M, Fadel E, Serraf A, Berrih-Aknin S, Le Panse R. Central role of interferon-beta in thymic events leading to myasthenia gravis. J Autoimmun. 2014 August; 52:44-52
[19] Benveniste E N, Qin H. Type I interferons as anti-inflammatory mediators. Sci STKE. 2007 Dec. 11; 2007 (416):pe70
[20] Margry B, Wieland W H, van Kooten P J, van Eden W, Broere F. Peritoneal cavity B-1a cells promote peripheral CD4+ T-cell activation. Eur J Immunol. 2013 September; 43(9):2317-26.
[21] Lövgren T, Eloranta M L, Båve U, Alm G V, Rönnblom L. Induction of interferon-alpha production in plasmacytoid dendritic cells by immune complexes containing nucleic acid released by necrotic or late apoptotic cells and lupus IgG. Arthritis Rheum. 2004 June; 50(6):1861-72.
[22] Balasa B, Deng C, Lee J, Christadoss P, Sarvetnick N. The Th2 cytokine IL-4 is not required for the progression of antibody-dependent autoimmune myasthenia gravis. J Immunol. 1998 Sep. 15; 161(6):2856-62.
[23] Ostlie N, Milani M, Wang W, Okita D, Conti-Fine B M. Absence of IL-4 facilitates the development of chronic autoimmune myasthenia gravis in C57BL/6 mice. J Immunol. 2003 Jan. 1; 170(1):604-12.
[24] Sun F, Ladha S S, Yang L, Liu Q, Shi S X, Su N, Bomprezzi R, Shi F D. Interleukin-10 producing-B cells and their association with responsiveness to rituximab in myasthenia gravis. Muscle Nerve. 2014 April; 49(4):487-94.
[25] Tian G, Li J L, Wang D G, Zhou D. Targeting IL-10 in auto-immune diseases. Cell Biochem Biophys. 2014 September; 70(1):37-49
[26] Cao Y, Amezquita R A, Kleinstein S H, Stathopoulos P, Nowak R J, O'Connor K C. Autoreactive T Cells from Patients with Myasthenia Gravis Are Characterized by Elevated IL-17, IFN-γ, and GM-CSF and Diminished IL-10 Production. J Immunol. 2016 Mar. 1; 196(5):2075-84.

[27] Aricha R, Mizrachi K, Fuchs S, Souroujon M C. Blocking of IL-6 suppresses experimental autoimmune myasthenia gravis. J Autoimmun. 2011 March; 36(2):135-41. Role of interleukin 10 transcriptional regulation in inflammation and autoimmune disease. Iyer S S, Cheng G. Crit Rev Immunol. 2012; 32(1):23-63.

What is claimed is:

1. A method of enhancing an immune response against a target antigen comprising administering to a subject an effective amount of a composition comprising an anti-BAFF receptor antibody or binding fragment thereof that is optionally bound or conjugated to an siRNA that targets BAFF receptor mRNA, wherein the composition is provided before, concurrently with, or after exposing the subject to the target antigen, wherein the composition is an adjuvant to an immunization, wherein the anti-BAFF receptor antibody or binding fragment thereof binds to a mature B cell, wherein the composition is formulated at a dose of 10 to 20 mg/Kg of total mammal body weight of the subject to stimulate an immune response.

2. The method of claim 1, further comprising the step of optimizing the dose of the composition to significantly increase antibody production against the target antigen by providing a first amount of the composition and after a pre-determined time measuring a first amount of antibody produced, and providing a second amount of the composition having more or less of the composition and measuring after the pre-determined time a second amount of antibody produced, and optionally, adjusting the amount of the composition one or more times until an optimal antibody production is obtained.

3. The method of claim 1, wherein the target antigen is a cancer antigen.

4. The method of claim 1, wherein the target antigen is a tumor associated antigen.

5. The method of claim 1, wherein the target antigen is an infectious disease antigen.

6. The method of claim 1, wherein the step of exposing the subject to the target antigen is administering a vaccine comprising the target antigen.

7. The method of claim 1, wherein the target antigen is a cancer antigen that is a tumor associated antigen (TAA) selected from the group consisting of carbonic anhydrase IX, α-fetoprotein (AFP), α-actinin-4, ART-4, B7, Ba 733, BAGE, CA125, CAMEL, CAP-1, CASP-8/m, CCL19, CCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD44, CD45, CD46, CD52, CD54, CD55, CD59, CD64, CD66a-e, CD67, CD70, CD70L, CD74, CD79a, CD80, CD83, CD95, CD126, CD132, CD133, CD138, CD147, CD154, CDCl$_2$7, CDK-4/m, CDKN2A, CEA, C3, C3a, C3b, C5a, C5, CTLA-4, CXCR4, CXCR7, CXCL12, HIF-1α, colon-specific antigen-p (CSAp), CEA (CEACAM-5), CEACAM-6, c-Met, DAM, EGFR, EGP-1 (TROP-2), EGP-2, ELF2-M, Ep-CAM, fibroblast growth factor (FGF), Flt-1, Flt-3, folate receptor, GAGE-1,2,8, GAGE-3,4,5,6,7; gp100, GRO-β, HLA-DR, human chorionic gonadotropin (HCG), HER2/neu, HMGB-1, hypoxia inducible factor (HIF-1), HSP70-2M, HST-2, Ia, IGF-1R, IFN-γ, IFN-α, IFN-β, IFN-λ1, IFN-λ2, IFN-λ3, IL-4R, IL-6R, IL-13R, IL-15R, IL-17R, IL-18R, IL-2, IL-6, IL-8, IL-12, IL-15, IL-17, IL-18, IL-23, IL-25, insulin-like growth factor-1 (IGF-1), Le-Y, LDR/FUT, macrophage migration inhibitory factor (MIF), MAGE-A1; MAGE-A2; MAGE-A3; MAGE-A4; MAGE-A6; MAGE-A9; MAGE-A10; MAGE-A12; MAGE-C2, MART-1, MART-2, NY-ESO-1, TRAG-3, mCRP, MCP-1, MIP-1A, MIP-1B, MIF, MUC1, MUC2, MUC3, MUC4, MUC5ac, MUC13, MUC16, MUM-1/2, MUM-3, NCA66, NCA95, NCA90, PD-1 receptor, placental growth factor, p53, PLAGL2, prostatic acid phosphatase, PSA, PRAIVIE, PRAME, PSMA, P1GF, ILGF, ILGF-1R, IL-6, IL-25, RS5, RANTES, SAGE, Sp17; SSX-2, SSX-4; survivin, TAC, TAG-72, tenascin, TRAIL receptor, TNF-α, Tn antigen, Thomson-Friedenreich antigens, tumor necrosis antigen, VEGF, ED-B fibronectin, WT-1, an angiogenesis marker, bcl-2, bcl-6, Kras, an oncogene marker, and an oncogene product.

8. The method of claim 1, wherein the BAFF receptor is a human BAFF receptor.

9. The method of claim 1, wherein the anti-BAFF receptor antibody or binding fragment and the siRNA that targets BAFF receptor mRNA are chemically cross-linked.

10. The method of claim 1, further comprising the step of chemically cross-linking the anti-BAFF receptor antibody or binding fragment and the siRNA that targets BAFF receptor mRNA with a linker that is at least one of: a conditionally self-cleaving RNA sequence, a pH sensitive linker, a hydrophobic sensitive linker, a cleavable linker, a linker that provides a sorting signal, a linker that reduces steric hindrance, a linker that contributes to a condensing ability of the nucleic acid binding domain, a peptide or protein linker, a protamine linker, a polyK linker, or an HIV-TaT protein translocation (TPTV) linker.

11. The method of claim 1, further comprising the step of chemically cross-linking the anti-BAFF receptor antibody or binding fragment and the siRNA that targets BAFF receptor mRNA using one or more of the following cross-linkers: glutaraldehyde, bissulfosuccinimidyl suberate, carbodiimide, bis(succinimidyl)penta(ethylene glycol), bis(succinimidyl) nona(ethylene glycol), bis(sulfosuccinimidyl) suberate, dimethyl suberimidate, an ethylene glycol characterized by formula (—$CH_2OH$—), wherein n is 2, 3, 4, 5, 6, 7, 8, 9, 10, 11, 12, 13, 14, 15, 16, 17, 18, 19, 20, 21, 22, 23, 24 or 25 and one or both termini of the ethylene glycol are substituted by a succinimide or maleimide group, N-(κ-Maleimidoundecanoyloxy) sulfosuccinimide ester, sulfosuccinimidyl (4-iodoacetyl) aminobenzoate, 1,8-bismaleimidodiethyleneglycol, or 1,11-bismaleimidotriethyleneglycol.

12. The method of claim 1, further comprising the step of adapting the composition for intravenous, intramuscular, oral, parenteral, enteral, intraperitoneal, pulmonary, nasal, subcutaneous, rectal, or transcutaneous administration.

13. The method of claim 1, wherein the anti-BAFF receptor antibody or binding fragment thereof is modified by affinity linkers and a protamine or a small basic protein.

14. The method of claim 1, wherein the anti-BAFF receptor antibody or binding fragment thereof is attached to a first affinity linker, and a protamine is attached to a second affinity linker, wherein the protamine is capable of binding a BAFF receptor-siRNA.

15. The method of claim 1, wherein the composition is provided in an amount sufficient to deplete BAFF receptor in at least one of peripheral blood mononuclear cells, lymph node cells, or splenocytes.

16. A method of treating or preventing myasthenia gravis comprising administering to a subject in need thereof a therapeutically or prophylactically effective amount of a composition comprising an anti-BAFF receptor antibody or binding fragment thereof that is bound or conjugated to an siRNA that targets BAFF receptor mRNA, wherein the anti-BAFF receptor antibody or binding fragment thereof binds to a mature B cell, wherein the composition is formulated at a dose of 2 to 6 mg/Kg of total mammal body weight of the subject to reduce an immune response.

17. The method of claim 16, wherein the BAFF receptor is a human BAFF receptor.

18. The method of claim 16, further comprising the step of optimizing the dose of the composition to reduce or eliminate the symptoms of myasthenia gravis in a human or an animal.

19. The method of claim 16, further comprising the step of optimizing the dose of the composition to not significantly reduce serum autoantibody or IFNγ level.

20. The method of claim 16, further comprising the step of optimizing the dose of the composition to induce significantly higher IL4 and IL10 levels.

21. A method of evaluating an adjuvant, the method comprising:
a) measuring at least one of antigen-specific antibodies from a blood sample obtained from a subject from a set of patients;
b) administering the adjuvant comprising an anti-BAFF receptor antibody or binding fragment thereof that is bound or optionally conjugated to an siRNA, an shRNA, or both, with affinity linkers, a small basic protein, or protamine that targets a BAFF receptor mRNA to a first subset of the patients, and a placebo to a second subset of the patients;
c) repeating step a) after the administration of the adjuvant or the placebo; and
d) determining if the adjuvant increases the levels of antibodies in the blood sample that is statistically significant as compared to any reduction occurring in the second subset of patients, wherein a statistically significant change indicates that the adjuvant is useful to increase antibody production.

22. The method of claim 21, further comprising the step of optimizing the dose of the composition to significantly increase antibody production against a target antigen.

23. The method of claim 21, wherein a target antigen is a cancer antigen that is a tumor associated antigen selected from the group consisting of carbonic anhydrase IX, α-fetoprotein (AFP), α-actinin-4, ART-4, B7, Ba 733, BAGE, CA125, CAMEL, CAP-1, CASP-8/m, CCL19, CCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD44, CD45, CD46, CD52, CD54, CD55, CD59, CD64, CD66a-e, CD67, CD70, CD70L, CD74, CD79a, CD80, CD83, CD95, CD126, CD132, CD133, CD138, CD147, CD154, CDC27, CDK-4/m, CDKN2A, CEA, C3, C3a, C3b, C5a, C5, CTLA-4, CXCR4, CXCR7, CXCL12, HIF-1α, colon-specific antigen-p (CSAp), CEA (CEACAM-5), CEACAM-6, c-Met, DAM, EGFR, EGP-1 (TROP-2), EGP-2, ELF2-M, Ep-CAM, fibroblast growth factor (FGF), Flt-1, Flt-3, folate receptor, GAGE-1,2,8, GAGE-3,4,5,6,7; gp100, GRO-β, HLA-DR, human chorionic gonadotropin (HCG), HER2/neu, HMGB-1, hypoxia inducible factor (HIF-1), HSP70-2M, HST-2, Ia, IGF-1R, IFN-γ, IFN-α, IFN-β, IFN-λ1, IFN-λ2, IFN-λ3, IL-4R, IL-6R, IL-13R, IL-15R, IL-17R, IL-18R, IL-2, IL-6, IL-8, IL-12, IL-15, IL-17, IL-18, IL-23, IL-25, insulin-like growth factor-1 (IGF-1), Le-Y, LDR/FUT, macrophage migration inhibitory factor (MIF), MAGE-A1; MAGE-A2; MAGE-A3; MAGE-A4; MAGE-A6; MAGE-A9; MAGE-A10; MAGE-A12; MAGE-C2, MART-1, MART-2, NY-ESO-1, TRAG-3, mCRP, MCP-1, MIP-1A, MIP-1B, MIF, MUC1, MUC2, MUC3, MUC4, MUC5ac, MUC13, MUC16, MUM-1/2, MUM-3, NCA66, NCA95, NCA90, PD-1 receptor, placental growth factor, p53, PLAGL2, prostatic acid phosphatase, PSA, PRAIVIE, PRAME, PSMA, P1GF, ILGF, ILGF-1R, IL-6, IL-25, RS5, RANTES, SAGE, Sp17; SSX-2, SSX-4; survivin, TAC, TAG-72, tenascin, TRAIL receptor, TNF-α, Tn antigen, Thomson-Friedenreich antigens, tumor necrosis antigen, VEGF, ED-B fibronectin, WT-1, an angiogenesis marker, bcl-2, bcl-6, Kras, an oncogene marker, and an oncogene product.

24. A method of evaluating a candidate drug in a composition believed to be useful at low dose in treating an autoimmune disease, the method comprising:
a) measuring at least one of autoantibody, IFNγ level, IL4 or IL10 levels from a blood sample or lymph node tissue obtained from a subject having the autoimmune disease from a set of patients;
b) administering a candidate drug comprising an anti-BAFF receptor antibody or binding fragment thereof that is optionally bound or conjugated to an siRNA, and shRNA, or both, that targets a BAFF receptor mRNA to a first subset of the patients, and a placebo to a second subset of the patients;
c) repeating step a) after the administration of the candidate drug or the placebo;
d) determining if the candidate drug reduces levels of autoantibody or IFNγ level, or increases the IL4 or IL10 levels that is statistically significant as compared to any reduction occurring in the second subset of patients, wherein a statistically significant change indicates that the candidate drug is useful in treating the autoimmune disease;

e) determining if the candidate drug increases levels of antigen specific antibody or type 1 IFN levels that is statistically significant as compared to increase in control subset of patients, wherein a statistically significant change indicates that the candidate is useful as an antimicrobial and anti-cancer immunomodulator or vaccine adjuvant.

25. The method of claim 24, wherein the composition is provided in a low dose of 2 to 6 mg/Kg of total mammal body weight.

26. The method of claim 24, wherein the composition is provided in a "high dose", as used herein, is a dose of 10 to 20 mg/Kg of total mammal body weight.

27. The method of claim 24, further comprising the step of raising or lowering the dose of the candidate drug to optimize the treatment of the autoimmune disease.

28. The method of claim 24, wherein the autoimmune disease is myasthenia gravis.

\* \* \* \* \*

SEQUENCE LISTING

<160> NUMBER OF SEQ ID NOS: 1

<210> SEQ ID NO 1
<211> LENGTH: 22
<212> TYPE: PRT
<213> ORGANISM: Artificial Sequence
<220> FEATURE:
<223> OTHER INFORMATION: Synthetic peptide

<400> SEQUENCE: 1

Arg Ser Gln Ser Arg Ser Arg Tyr Tyr Arg Gln Arg Gln Arg Ser Arg
1               5                   10                  15

Arg Arg Arg Arg Arg Ser
            20